United States Patent
Okuda et al.

(10) Patent No.: US 7,473,544 B2
(45) Date of Patent: Jan. 6, 2009

(54) ALKALINE PROTEASE

(75) Inventors: Mitsuyoshi Okuda, Haga-gun (JP); Tsuyoshi Sato, Haga-gun (JP); Yasushi Takimura, Haga-gun (JP); Nobuyuki Sumitomo, Haga-gun (JP); Tohru Kobayashi, Haga-gun (JP)

(73) Assignee: Kao Corporation, Tokyo (JP)

( * ) Notice: Subject to any disclaimer, the term of this patent is extended or adjusted under 35 U.S.C. 154(b) by 103 days.

(21) Appl. No.: 11/235,249

(22) Filed: Sep. 27, 2005

(65) Prior Publication Data

US 2006/0078978 A1    Apr. 13, 2006

(30) Foreign Application Priority Data

Oct. 8, 2004    (JP)    ............... 2004-297023

(51) Int. Cl.
*C12N 9/64*    (2006.01)
*C11D 3/386*    (2006.01)

(52) U.S. Cl. .................... 435/226; 510/300
(58) Field of Classification Search ........... None
See application file for complete search history.

(56) References Cited

U.S. PATENT DOCUMENTS

| | | | | |
|---|---|---|---|---|
| 5,891,701 A * | 4/1999 | Sloma et al. | ........... | 435/221 |
| 6,376,227 B1 | 4/2002 | Takaiwa et al. | | |
| 6,759,228 B2 * | 7/2004 | Takaiwa et al. | ........... | 435/220 |
| 2004/0002432 A1 | 1/2004 | Okuda et al. | | |

FOREIGN PATENT DOCUMENTS

| | | |
|---|---|---|
| EP | 1 029 920 A1 | 8/2000 |
| EP | 1 209 233 A2 | 5/2002 |
| EP | 1 347 044 A2 | 9/2003 |
| EP | 1 466 970 A1 | 10/2004 |
| JP | 2004-122 A | 1/2004 |
| JP | 2004-57195 A | 2/2004 |
| WO | WO 98/56927 | 12/1998 |
| WO | WO 99/18218 | 4/1999 |
| WO | WO 00/37627 | 6/2000 |
| WO | WO 02/31133 A1 | 4/2002 |
| WO | WO 2004/083362 A2 | 9/2004 |

OTHER PUBLICATIONS

Galye et al, Identification of regions in interleukin-1 alpha important for activity. J Biol Chem. Oct. 15, 1993;268(29):22105-11.*
Whisstock et al, Prediction of protein function from protein sequence and structure. Q Rev Biophys. Aug. 2003;36(3);307-40. Review.*
Ito et al, Alkaline detergent enzymes from alkaliphiles: enzymatic properties, genetics, and structures. Extremophiles (1998) 2(3):185-190.*
Katsuhisa Saeki, et al., "Novel Oxidatively Stable Subtilisin-like Serine Proteases from Alkaliphilic *Bacillus* spp.: Enzymatic Properties, Sequences, and Evolutionary Relationships", Biochemical and Biophysical Research Communications vol. 279, No. 2, 2000, pp. 313-319.

* cited by examiner

*Primary Examiner*—Sheridan Swope
(74) *Attorney, Agent, or Firm*—Oblon, Spivak, McClelland, Maier & Neustadt, P.C.

(57) ABSTRACT

The present invention provides an alkaline protease exhibiting high detergency and productivity, which is obtained by further enhancing the detergency of an alkaline protease effective against complex dirt and enhancing the specific activity.

6 Claims, 7 Drawing Sheets

Fig. 1

```
KP43    1:NDVARGIVKADVAQSSYGLYGQGQIVAVADTGLDTGRNDSSMHEAFRGKITALYALGRTNNANDTNGHGTHVAGSVLGNGSTNKGMAPQA  90
KP9860  1:NDVARGIVKADVAQSSYGLYGQGQIVAVADTGLDTGRNDSSMHEAFRGKITALYALGRTNNANDTNGHGTHVAGSVLGNGATNKGMAPQA  90
E-1     1:NDVARGIVKADVAQNNYGLYGQGQVVAVADTGLDTGRNDSSMHEAFRGKITALYALGRTNNANDPNGHGTHVAGSVLGNALNKG-MAPQA  89
Ya      1:NDVARGIVKADVAQNNYGLYGQGQVVAVADTGLDTGRNDSSMHEAFRGKITALYALGRTNNASDPNGHGTHVAGSVLGNALNKG-MAPQA  89
SD-521  1:NDVARGIVKADVAQNNYGLYGQGQVVAVADTGLDTGRNDSSMHEAFRGKITALYALGRTNNANDPNGHGTHVAGSVLGNALNKG-MAPQA  89
A-1     1:NDVARGIVKADVAQSSYGLYGQGQVVAVADTGLDTGRNDSSMHEAFRGKITAIYALGRTNNANDPNGHGTHVAGSVLGNGTSNKGMAPQA  90
A-2     1:NDVARGIVKADVAQNNFGLYGQGQIVAVADTGLDTGRNDSSMHEAFRGKITALYALGRTNNANDPNGHGTHVAGSVLGNATNK-GMAPQA  89
9865    1:NDVARGIVKADVAQSSYGLYGQGQIVAVADTGLDTGRNDSSMHEAFRGKITALYALGRTNNANDTNGHGTHVAGSVLGNGSTNKGMAPQA  90
          ************* .******  ******************************.********.*.************** .*****

KP43    91:NLVFQSIMDSGGGLGGLPSNLQTLFSQAYSAGARIHTNSWGAAVNGAYTTDSRNVDDYVRKNDMTILFAAGNEGPNGGTISAPGTAKNAI  180
KP9860  91:NLVFQSIMDSSGGLGGLPSNLQTLFSQAFSAGARIHTNSWGAAVNGAYTTDSRNVDDYVRKNDMTILFAAGNEGPNGGTISAPGTAKNAI  180
E-1     90:NLVFQSIMDSSGGLGGLPSNLNTLFSQAWNAGARIHTNSWGAPVNGAYTANSRQVDEYVRNNDMTVLFAAGNEGPNSGTISAPGTAKNAI  179
Ya      90:NLVFQSIMDSSGGLGGLPSNLNTLFSQAWNAGARIHTNSWGAPVNGAYTANSRQVDEYVRNNDMTVLFAAGNEGPNSGTISAPGTAKNAI  179
SD-521  90:NLVFQSIMDSSGGLGGLPSNLNTLFSQAWNAGARIHTNSWGAPVNGAYTANSRQVDEYVRNNDMTVLFAAGNEGPNSGTISAPGTAKNAI  179
A-1     91:NLVFQSVMDSNGGLGGLPSNVSTLFSQAYSAGARIHTNSWGAPVNGAYTTDSRNVDDYVRKNDMAVLFAAGNEGPNGGTISAPGTAKNAI  180
A-2     90:NLVFQSIMDSGGGLGGLPANLQTLFSQAYSAGARIHTNSWGAPVNGAYTTDSRNVDDYVRKNDMTILFAAGNEGPGSGTISAPGTAKNAI  179
9865    91:NLVFQSIMDSGGGLGGLPSNLQTLFSQAYSAGARIHTNSWGAAVNGAYTTDSRNVDDYVRKNDMTILFAAGNEGPNGGTISAPGTAKNAI  180
          ******.*** ******.*. ****** .************.*****..**.**.***.***. **********. *************

KP43    181:TVGATENLRPSFGSYADNINHVAQFSSRGPTKDGRIKPDVMAPGTFILSARSSLAPDSSFWANHDSKYAYMGGTSMATPIVAGNVAQLRE  270
KP9860  181:TVGATENLRPSFGSYADNINHVAQFSSRGPTKDGRIKPDVMAPGTYILSARSSLAPDSSFWANHDSKYAYMGGTSMATPIVAGNVAQLRE  270
E-1     180:TVGATENYRPSFGSIADNPNHIAQFSSRGATRDGRIKPDVTAPGTFILSARSSLAPDSSFWANYNSKYAYMGGTSMATPIVAGNVAQLRE  269
Ya      180:TVGATENYRPSFGSIADNPNHIAQFSSRGATRDGRIKPDVTAPGTFILSARSSLAPDSSFWANYNSKYAYMGGTSMATPIVAGNVAQLRE  269
SD-521  180:TVGATENYRPSFGSIADNPNHIAQFSSRGATRDGRIKPDVTAPGTFILSARSSLAPDSSFWANYNSKYAYMGGTSMATPIVAGNVAQLRE  269
A-1     181:TVGATENLRPSFGSYADNINHVAQFSSRGPTKDGRIKPDVMAPGTFILSARSSLAPDSSFWANHDSKYAYMGGTSMATPIVAGNVAQLRE  270
A-2     180:TVGATENLRPSFGSYADNINHVAQFSSRGPTRDGRIKPDVMAPGTYILSARSSLAPDSSFWANHDSKYAYMGGTSMATPIVAGNVAQLRE  269
9865    181:TVGATENLRPSFGSYADNINHVAQFSSRGPTKDGRIKPDVMAPGTFILSARSSLAPDSSFWANHDSKYAYMGGTSMATPIVAGNVAQLRE  270
          *******.******.***.**.*******.* ********.****.****************..************************

KP43    271:HFVKNRGITPKPSLLKAALIAGAADIGLGYPNGNQGWGRVTLDKSLNVAYVNESSSLSTSQKATYSFTATAGKPLKISLVNSDAPASTTA  360
KP9860  271:HFVKNRGITPKPSLLKAALIAGAADVGLGYPNGNQGWGRVTLDKSLNVAYVNESSALSTSQKATYTFTATAGKPLKISLVNTDAPGSTTA  360
E-1     270:HFIKNRGITPKPSLIKAALIAGATDVGLGYPSGDQGWGRVTLDKSLNVAYVNEATALTTGQKATYSFQTQAGKPLKISLVNTDAPGSTTA  359
Ya      270:HFIKNRGITPKPSLIKAALIAGATDVGLGYPNGDQGWGRVTLDKSLNVAYVNEATALATGQKATYSFQAQAGKPLKISLVNTDAPGSTTA  359
SD-521  270:HFIKNRGITPKPSLIKAALIAGATDVGLGYPSGDQGWGRVTLDKSLNVAYVNEATALATGQKATYSFQAQAGKPLKISLVNTDAPGSTTA  359
A-1     271:HFIKNRGITPKPSLLKAALIAGATDIGLGYPSGNQGWGRVTLDKSLNVAFVNETSSLSTNQKATYSFTAQSGKPLKISLVNSDAPASTSA  360
A-2     270:HFVKNRGVTPKPSLLKAALIAGAADVGLGFPNGNQGWGRVTLDKSLNVAFVNETSPLSTSQKATYSFTAQAGKPLKISLVNSDAPGSTTA  359
9865    271:HFVKNRGITPKPSLLKAALIAGAADIGLGYPNGNQGWGRVTLDKSLNVAYVNESSSLSTSQKATYSFTATAGKPLKISLVNSDAPASTTA  360
          ** ****.******.********* .***.*.*.*********.****.***.  .*.*.*****.*....*********.****.***

KP43    361:SVTLVNDLDLVITAPNGTQYVGNDFTSPYNDNWDGRNNVENVFINAPQSGTYTIEVQAYNVPVGPQTFSLAIVN                 434
KP9860  361:SVTLVNDLDLVITAPNGTRYVGNDFSAPFDNNWDGRNNVENVFINSPQSGTYTIEVQAYNVPVGPQNFSLAIVN                 434
E-1     360:SYTLVNDLDLVITAPNGQKYVGNDFSYPYDNNWDGRNNVENVFINAPQSGTYIIEVQAYNVPSGPQRFSLAIVH                 433
Ya      360:SYTLVNDLDLVITAPNGQKYVGNDFSYPYDNNWDGRNNVENVFINAPQSGTYIIEVQAYNVPSGPQRFSLAIVH                 433
SD-521  360:SYTLVNDLDLVITAPNGQKYVGNDFSYPYDNNWDGRNNVENVFINAPQSGTYTIEVQAYNVPSGPQRFSLAIVH                 433
A-1     361:SVTLVNDLDLVITAPNGTKYVGNDFTAPYDNNWDGRNNVENVFINAPQSGTYTVEVQAYNVPQGPQAFSLAIVN                 434
A-2     360:SLTLVNDLDLVITAPNGTKYVGNDFTAPYDNNWDGRNNVENVFINAPQSGTYTVEVQAYNVPVSPQTFSLAIVH                 433
9865    361:SVTLVNDLDLVITAPNGTQYVGNDFTSPYNNNWDGRNNVENVFINAPQSGTYTIEVQAYNVPVGPQTFSLAIVN                 434
          * ****************..******* ..****************.*******.********.*** *******
```

Fig. 2-1
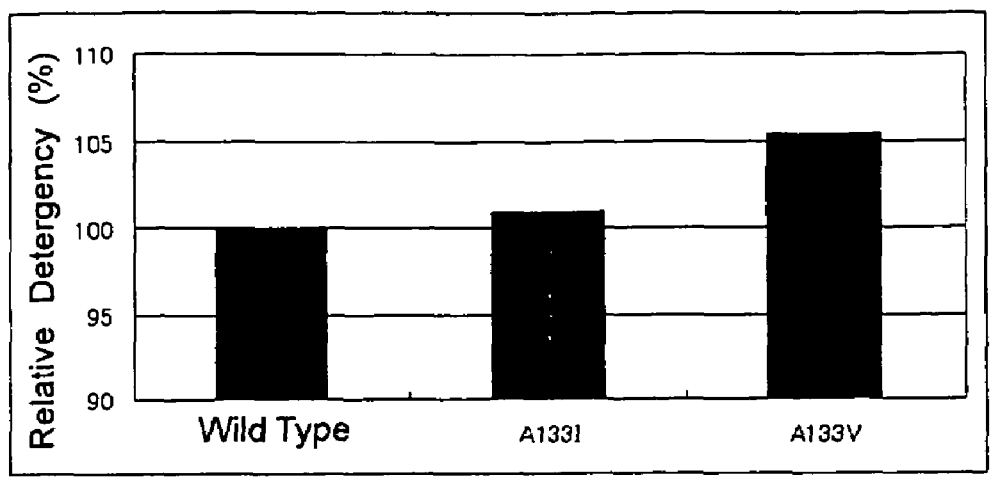
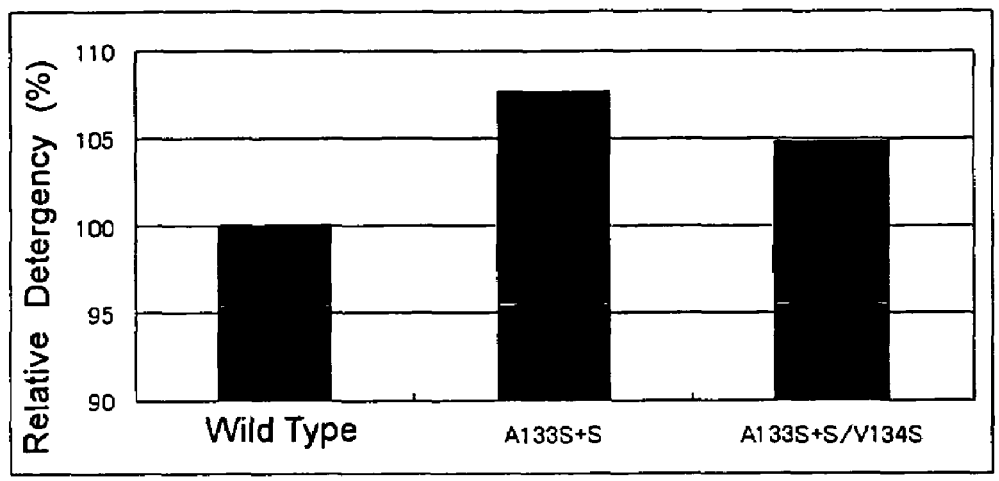
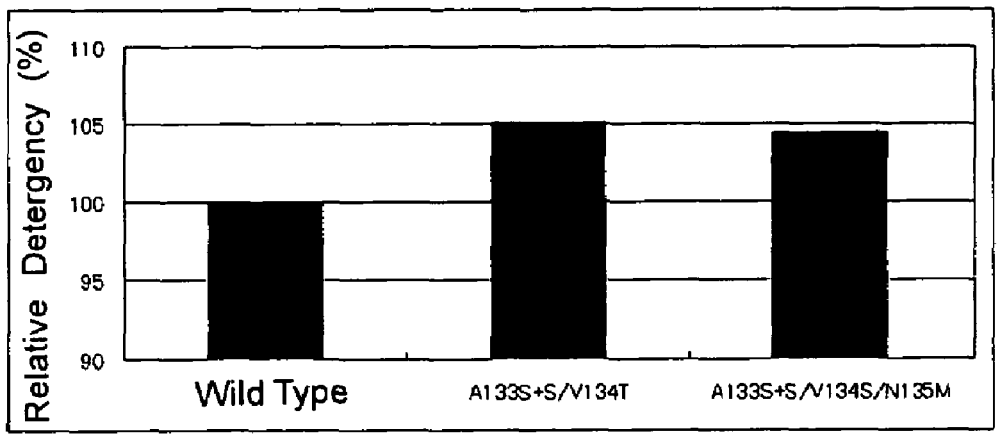

Fig. 2-3
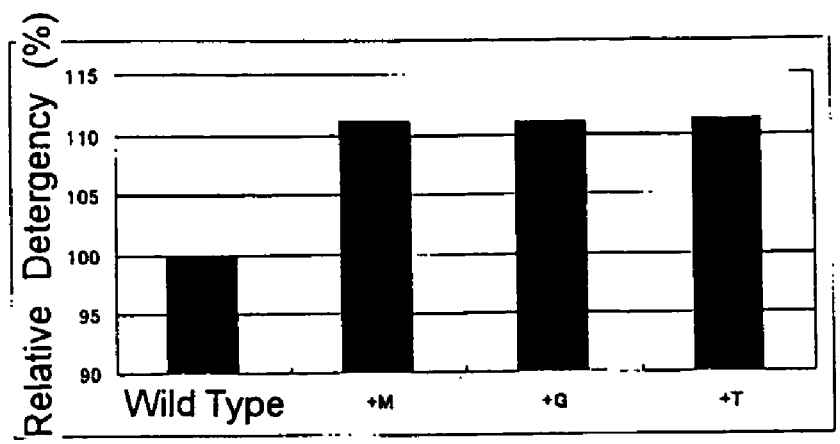
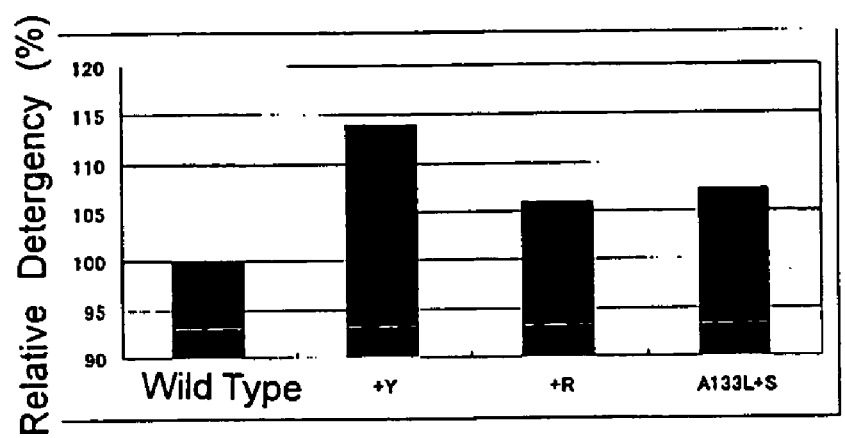
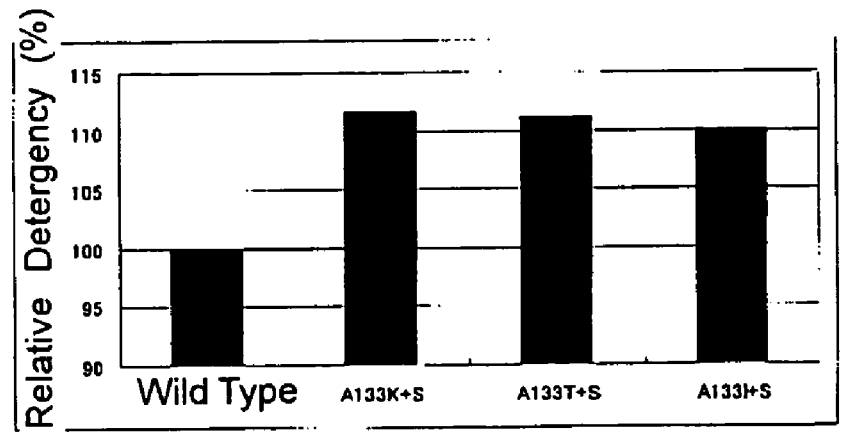

Fig. 2-5
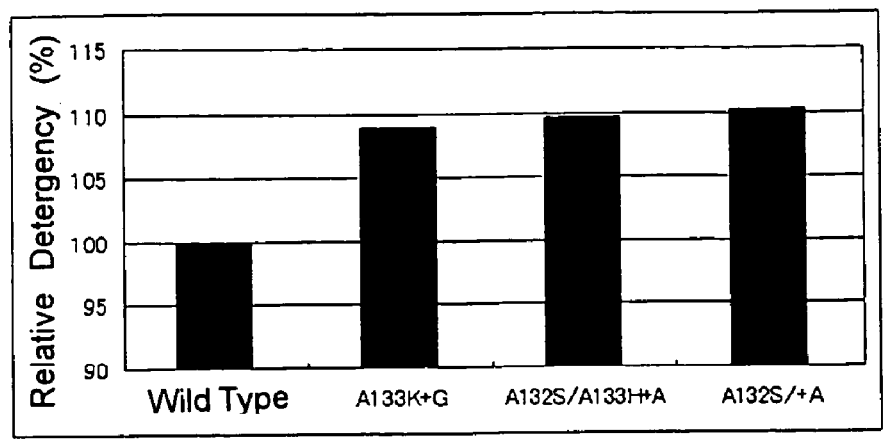
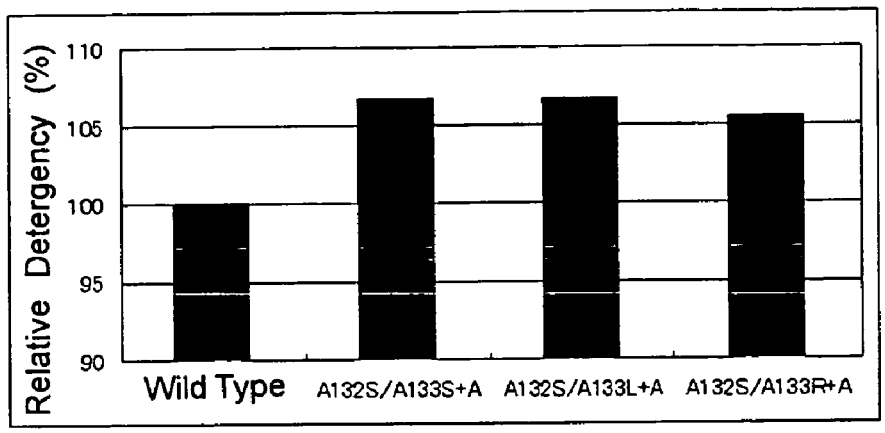
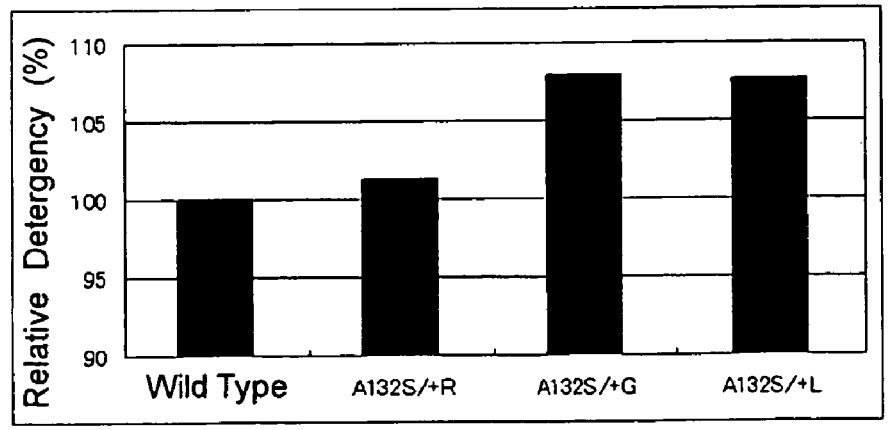

Fig. 2-6
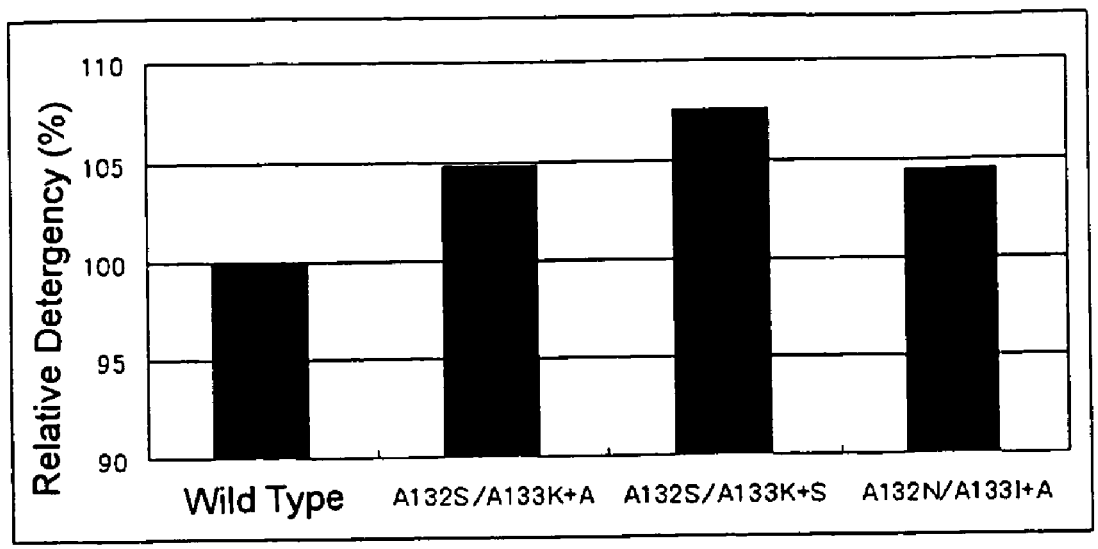
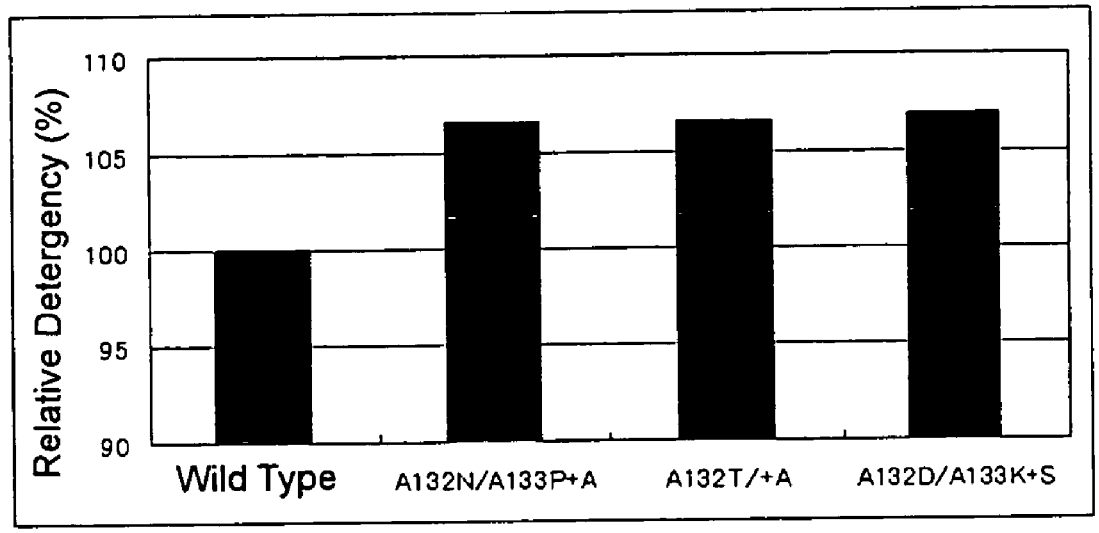

ALKALINE PROTEASE

FIELD OF THE INVENTION

The present invention relates to an alkaline protease which is useful as an enzyme to be incorporated into a detergent, to a gene encoding the alkaline protease, and to a detergent composition containing the alkaline protease.

BACKGROUND OF THE INVENTION

Proteases have long been employed in industry; i.e., in a wide variety of products, including detergents (e.g., laundry detergents), fiber-modifying agents, leather treatment agents, cosmetics, bath agents, food-modifying agents, and drugs. Proteases for detergents are industrially produced in the greatest amounts. Examples of such proteases known heretofore include Alcalase, Savinase (registered trademark; Novozymes), Maxacal (registered trademark; Genencor), Blap (registered trademark; Henkel), and KAP (Kao Corporation).

Protease is incorporated into a laundry detergent for providing the detergent with the ability to degrade dirt, whose main component is protein, deposited on clothing into low-molecular-weight products, thereby promoting solubilization of the thus-degraded products with a surfactant. However, in actuality, such deposited dirt are complex dirt containing, in addition to proteins, a plurality of organic and inorganic components such as sebum-derived lipid and solid particles. Therefore, a demand continues to exist for a detergent exhibiting excellent detergency to such complex dirt.

In view of the foregoing, the present inventors have discovered several alkaline proteases having a molecular weight of about 43,000, which maintain sufficient casein-degrading activity even in the presence of a fatty acid of high concentration and which exhibit excellent detergency to complex dirt containing proteins and sebum; and have previously applied for a patent on the alkaline proteases (see International Publication WO99/18218 pamphlet). These alkaline proteases differ from conventionally known subtilisin, a serine protease derived from bacteria belonging to the genus *Bacillus*, in molecular weight, primary structure, and enzymological characteristics, and in a property that it has a very strong oxidizer resistance. These alkaline proteases are suggested to be classified into a new subtilisin subfamily (see Saeki, et al., Biochem. Biophys. Res. Commun., 279, 313-319, 2000).

Although the aforementioned alkaline proteases exhibit high detergency to complex dirt containing sebum dirt, etc., demand has arisen for a protease exhibiting further enhanced detergency. Mass production of such a protease exhibiting excellent detergency on an industrial scale requires enhancement of productivity thereof. Examples of the method for such productivity enhancement include a method for improving protease-producing bacteria through mutation; a method for modifying a gene encoding such a protease, or a gene involved in control of expression of the protease, thereby enhancing the amount of the protein to be secreted; and a method for modifying a gene encoding such a protease, thereby enhancing the specific activity of the protease. Thus, the present inventors have conducted studies on modification of genes encoding the aforementioned alkaline proteases, and have discovered a mutant alkaline protease exhibiting enhanced protein secretion ability and specific activity (see JP-A-2004-000122 and 2004-057195).

However, mass production of the enzyme at low cost requires further enhanced production efficiency, and thus the enzyme is required to be secreted in a large amount, not to mention that it has enhanced specific activity and detergency.

SUMMARY OF THE INVENTION

The present invention provides an alkaline protease which is obtained by applying one or more of the below-described modifications (a) through (e); i.e., amino acid residue substitution and/or insertion to an alkaline protease having the amino acid sequence of SEQ ID NO: 3 or an alkaline protease that is functionally equivalent thereto, and which exhibits a specific activity and/or detergency higher than that of the alkaline protease having the amino acid sequence of SEQ ID NO: 3:

(a) substitution, with an amino acid residue, of the amino acid residue at position 133 or at a position corresponding thereto;

(b) insertion of an amino acid residue between the amino acid residues at positions 133 and 134 or at positions corresponding thereto;

(c) substitution, with an amino acid residue, of the amino acid residue at original position 134 (as used herein, the "original position" refers to the position before insertion) or at a position corresponding thereto;

(d) substitution, with an amino acid residue, of the amino acid residue at original position 135 or at a position corresponding thereto; and (e) substitution, with an amino acid residue, of the amino acid residue at position 132 or at a position corresponding thereto.

The present invention also provides a gene encoding the alkaline protease; a vector containing the gene; and a transformant containing the vector.

The present invention also provides a detergent composition containing the alkaline protease.

BRIEF DESCRIPTION OF THE DRAWINGS

FIG. 1 shows alignment of amino acid sequences of proteases (SEQ ID NOs: 19-25) that have high identity with the amino acid sequence of SEQ ID NO: 3.

FIG. 2-1 shows detergency of alkaline proteases of the present invention.

FIG. 2-2 shows detergency of alkaline proteases of the present invention.

FIG. 2-3 shows detergency of alkaline proteases of the present invention.

FIG. 2-4 shows detergency of alkaline proteases of the present invention.

FIG. 2-5 shows detergency of alkaline proteases of the present invention.

FIG. 2-6 shows detergency of alkaline proteases of the present invention.

DETAILED DESCRIPTION OF THE INVENTION

Figure 2:
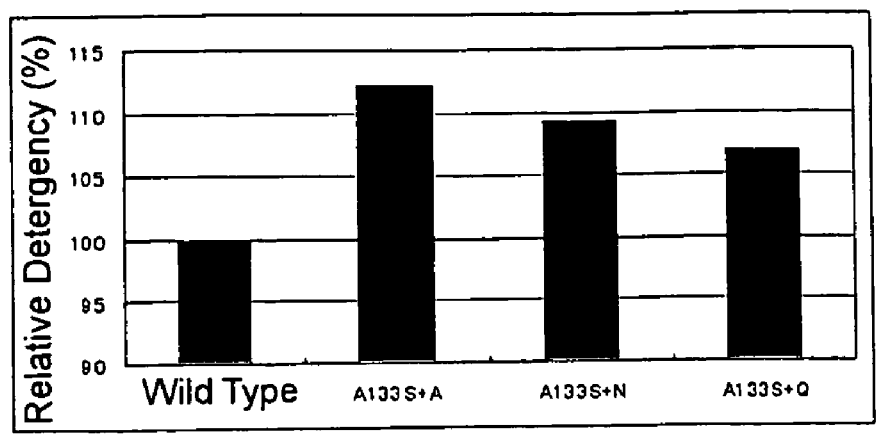
Figure 2:
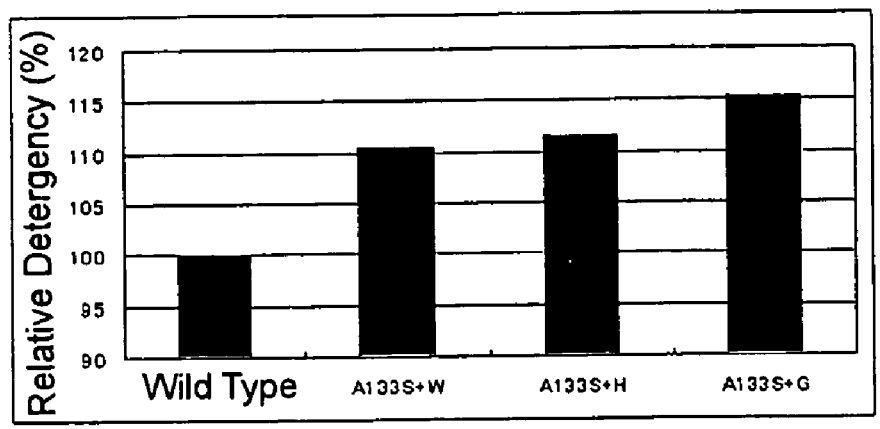
Figure 2:
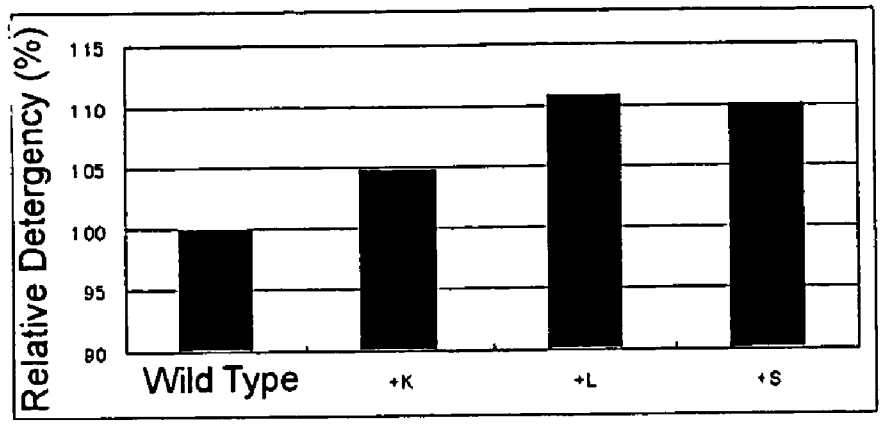
Figure 2:
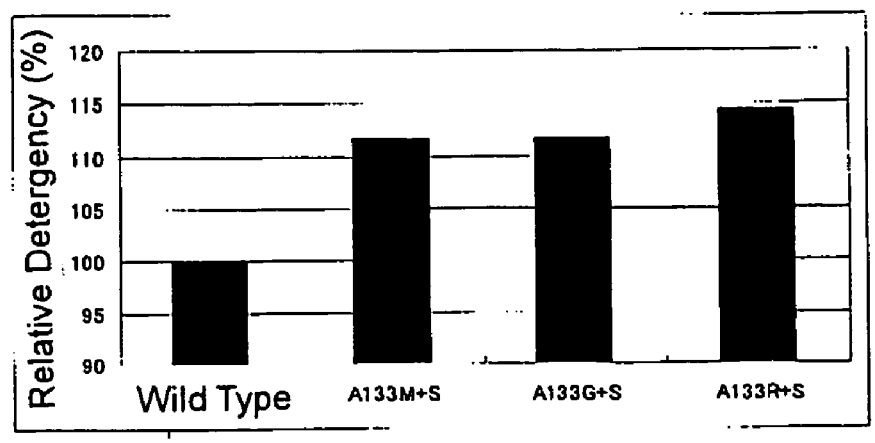

The present invention provides an alkaline protease exhibiting high detergency and productivity, which is obtained by further enhancing the detergency of an alkaline protease effective against complex dirt and enhancing the specific activity of the enzyme.

The present inventors have made an attempt to appropriately align amino acid sequences of the alkaline proteases (molecular weight: about 43,000) which are suggested to be classified into a new subtilisin subfamily, to thereby select amino acids to be modified, and have subjected the amino acids to site-directed modification; for example, substitution with an arbitrary amino acid, or insertion or deletion of an arbitrary amino acid. As a result, the present inventors have found that enhancing the specific activity of an alkaline protease requires a specific amino acid residue at a specific position of the amino acid sequence thereof. The present inventors have also found that enhancing the detergency of an alkaline protease requires insertion of a specific amino acid residue between specific positions of the amino acid sequence thereof.

According to the present invention, there can be provided an alkaline protease suitable for incorporation into a detergent, which is obtained by enhancing the detergency and specific activity of an alkaline protease exhibiting excellent detergency to complex dirt.

The alkaline protease of the present invention is obtained by applying one or more of the below-described modifications (a) through (e); i.e., amino acid residue substitution and/or insertion to an alkaline protease having the amino acid sequence of SEQ ID NO: 3 or an alkaline protease that is functionally equivalent thereto:

(a) substitution, with an amino acid residue, of the amino acid residue at position 133 or at a position corresponding thereto;

(b) insertion of an amino acid residue between the amino acid residues at positions 133 and 134 or at positions corresponding thereto;

(c) substitution, with an amino acid residue, of the amino acid residue at original position 134 or at a position corresponding thereto;

(d) substitution, with an amino acid residue, of the amino acid residue at original position 135 or at a position corresponding thereto; and (e) substitution, with an amino acid residue, of the amino acid residue at position 132 or at a position corresponding thereto. Preferably, the alkaline protease of the present invention exhibits a specific activity or detergency higher than that of the alkaline protease having the amino acid sequence of SEQ ID NO: 3, and more preferably, the former alkaline protease exhibits a specific activity and detergency higher than those of the latter alkaline protease.

The alkaline protease of the present invention may be of a wild type, or may be a wild-type mutant protease or an artificially mutated protease.

Preferred examples of the combination of two or more of the above-described modifications (a) through (e) (amino acid residue substitution and/or insertion) include combinations described below in 1) through 5):

1) combination of an amino acid residue substitution of modification (a) and an amino acid residue insertion of modification (b);

2) combination of an amino acid residue substitution of modification (a), an amino acid residue insertion of modification (b), and an amino acid residue substitution of modification (c);

3) combination of an amino acid residue substitution of modification (a), an amino acid residue insertion of modification (b), an amino acid residue substitution of modification (c), and an amino acid residue substitution of modification (d);

4) combination of an amino acid residue substitution of modification (a), an amino acid residue insertion of modification of (b), and an amino acid residue substitution of modification of (e); and 5) combination of an amino acid residue insertion of modification (b) and an amino acid residue substitution of modification (e).

Preferred specific examples of the alkaline protease of the present invention include alkaline proteases described below in 6) through 16):

6) an alkaline protease obtained through an amino acid residue substitution of modification (a), in which the introduced amino acid residue by way of substitution may be lysine, threonine, asparagine, glutamine, valine, leucine, or isoleucine;

7) an alkaline protease obtained through an amino acid residue insertion of modification (b), in which the inserted amino acid residue may be lysine, leucine, serine, methionine, glycine, threonine, tyrosine, or arginine;

8) an alkaline protease obtained through combination of an amino acid residue substitution of modification (a) and an amino acid residue insertion of modification (b), in which (a) introduced amino acid residue/(b) inserted amino acid residue may be (a) proline/(b) isoleucine, (a) leucine/(b) serine, (a) leucine/(b) glycine, (a) leucine/(b) threonine, (a) serine/(b) alanine, (a) serine/(b) asparagine, (a) serine/(b) glutamine, (a) serine/(b) tryptophan, (a) serine/(b) histidine, (a) serine/(b) glycine, (a) lysine/(b) serine, (a) threonine/(b) serine, (a) isoleucine/(b) serine, (a) methionine/(b) serine, (a) glycine/(b) serine, (a) arginine/(b) serine, (a) glutamic acid/(b) serine, (a) asparagine/(b) serine, (a) phenylalanine/(b) serine, (a) tryptophan/(b) serine, (a) lysine/(b) alanine, (a) arginine/(b) alanine, (a) lysine/(b) glycine, or (a) serine/(b) serine;

9) an alkaline protease obtained through combination of an amino acid residue substitution of modification (a), an amino acid residue insertion of modification (b), and an amino acid residue substitution of modification (c), in which (a) introduced amino acid residue/(b) inserted amino acid residue/(c) introduced amino acid residue may be (a) serine/(b) serine/(c) threonine, serine, glycine, or alanine;

10) an alkaline protease obtained through combination of an amino acid residue substitution of modification (a), an amino acid residue insertion of modification (b), an amino acid residue substitution of modification (c), and an amino acid residue substitution of modification (d), in which (a) introduced amino acid residue/(b) inserted amino acid residue/(c) introduced amino acid residue/(d) introduced amino acid residue may be (a) serine/(b) serine/(c) serine/(d) alanine, (a) serine/(b) serine/(c) serine/(d) arginine, or (a) serine/(b) serine/(c) serine/(d) methionine;

11) an alkaline protease obtained through combination of an amino acid residue substitution of modification (a), an amino acid residue insertion of modification (b), and an amino acid residue substitution of modification (e), in which (a) introduced amino acid residue/(b) inserted amino acid residue/(e) introduced amino acid residue may be (a) serine/(b) serine/(e) serine, (a) serine/(b) serine/(e) glutamine, or (a) serine/(b) serine/(e) methionine;

12) an alkaline protease obtained through combination of an amino acid residue insertion of modification (b) and an amino acid residue substitution of modification (e), in which (b) inserted amino acid residue/(e) introduced amino acid residue may be (b) alanine, arginine, glycine, or leucine/(e) serine;

13) an alkaline protease obtained through combination of an amino acid residue substitution of modification (a), an amino acid residue insertion of modification (b), and an amino acid residue substitution of modification (e), in which (a) introduced amino acid residue/(b) inserted amino acid residue/(e) introduced amino acid residue may be (a) isoleucine/(b) alanine/(e) serine, (a) histidine/(b) alanine/ (e) serine, (a) serine/(b) alanine/ (e) serine, (a) leucine/(b) alanine/(e)

serine, (a) arginine/(b) alanine/(e) serine, (a) lysine/(b) alanine/(e) serine, or (a) lysine/(b) serine/(e) serine;

14) an alkaline protease obtained through combination of an amino acid residue substitution of modification (a), an amino acid residue insertion of modification (b), and an amino acid residue substitution of modification (e), in which (a) introduced amino acid residue/(b) inserted amino acid residue/(e) introduced amino acid residue may be (a) isoleucine/(b) alanine/(e) asparagine or (a) proline/(b) alanine/(e) asparagine;

15) an alkaline protease obtained through combination of an amino acid residue insertion of modification (b) and an amino acid residue substitution of modification (e), in which (b) inserted amino acid residue/(e) introduced amino acid residue may be (b) alanine/(e) methionine or threonine; and 16) an alkaline protease obtained through combination of an amino acid residue substitution of modification (a), an amino acid residue insertion of modification (b), and an amino acid residue substitution of modification (e), in which (a) introduced amino acid residue/(b) inserted amino acid residue/(e) introduced amino acid residue may be (a) lysine/(b) serine/(e) asparagine or isoleucine.

Examples of the alkaline protease having the amino acid sequence of SEQ ID NO: 3 include protease KP43 [derived from *Bacillus* sp. KSM-KP43 (FERM BP-6532), WO99/18218, GenBank Accession No. AB051423].

The alkaline protease that is functionally equivalent to the alkaline protease having the amino acid sequence of SEQ ID NO: 3 may be a wild-type alkaline protease or a wild-type mutant alkaline protease. Examples of the functionally equivalent alkaline protease include an alkaline protease having an amino acid sequence obtained through deletion, substitution, or addition of one to several amino acid residues at positions other than position 132, 133, 134, or 135 of the amino acid sequence of SEQ ID NO: 3 or a position corresponding thereto; and an alkaline protease having an amino acid sequence having an identity of 80% or more, preferably 87% or more, even more preferably 90% or more, still more preferably 95% or more, further still more preferably 98%, with the amino acid sequence of SEQ ID NO: 3, which alkaline proteases exhibit characteristics similar to those of the alkaline protease having the amino acid sequence of SEQ ID NO: 3. Preferably, the alkaline protease has the following characteristics: acting within an alkaline region (at a pH of 8 or higher), exhibiting oxidizer resistance, exhibiting 80% or more residual activity when treated at 50° C. and a pH of 10 for 10 minutes, being inhibited by diisopropyl fluorophosphate (DFP) and phenylmethanesulfonyl fluoride (PMSF), and having a molecular weight of 43,000±2,000 as determined by SDS-PAGE. As used herein, the expression "the alkaline protease exhibits oxidizer resistance" refers to the case where, after the alkaline protease is allowed to stand at 30° C. for 20 minutes in a 20 mM Britton-Robinson buffer (pH 10) containing hydrogen peroxide (50 mM) and calcium chloride (5 mM), the alkaline protease exhibits at least 50% residual activity.

Examples of the alkaline protease having an amino acid sequence having 80% or more identity with the amino acid sequence of SEQ ID NO: 3 include protease KP9860 [derived from *Bacillus* sp. KSM-KP9860 (FERM BP-6534), WO99/18218, GenBank Accession No. AB046403; SEQ ID NO: 19]; protease E-1 [derived from *Bacillus* No. D-6 (FERM P-1592), JP-A-49-71191, GenBank Accession No. AB046402; SEQ ID NO: 20]; protease Ya [derived from *Bacillus* sp.Y (FERM BP-1029), JP-A-61-280268, GenBank Accession No. AB046404; SEQ ID NO: 21]; protease SD521 [derived from *Bacillus* SD521 (FERM P-11162), JP-A-3-191781, GenBank Accession No. AB046405; SEQ ID NO: 22]; protease A-1 [derived from NCIB12289, WO88/01293, GenBank Accession No. AB046406; SEQ ID NO: 23]; protease A-2 [derived from NCIB12513, WO98/56927; SEQ ID NO: 24]; protease 9865 [derived from *Bacillus* sp. KSM-9865 (FERM P-18566), GenBank Accession No. AB084155; SEQ ID NO: 25]; mutant proteases described in JP-A-2002-218989, 2002-306176, 2003-125783, 2004-000122, and 2004-057195; a mutant obtained through substitution of position 63 of the amino acid sequence of SEQ ID NO: 3 with serine, a mutant obtained through substitution of position 89 with histidine, a mutant obtained through substitution of position 120 with arginine, a mutant obtained through substitution of positions 63 and 187 with serine, a mutant obtained through substitution of position 226 with tyrosine, a mutant obtained through substitution of position 296 with valine, and a mutant obtained through substitution of position 304 with serine (JP-A-2004-305175); and a mutant obtained through substitution of position 15 of the amino acid sequence of SEQ ID NO: 3 with histidine, a mutant obtained through substitution of position 16 with threonine or glutamine, a mutant obtained through substitution of position 166 with glycine, a mutant obtained through substitution of position 167 with valine, a mutant obtained through substitution of position 346 with arginine, and a mutant obtained through substitution of position 405 with aspartic acid (JP-A-2004-305176).

The identity between amino acid sequences is calculated through the Lipman-Pearson method (Science, 227, 1435, (1985)). Specifically, the identity is calculated through analysis by use of a Search homology program of genetic information processing software Genetyx-Win (Ver. 5.1.1; Software Development Co., Ltd.), wherein unit size to compare (ktup) is taken as 1.

In the present invention, "an amino acid residue at a corresponding position" can be identified by comparing amino acid sequences of alkaline proteases through a known algorithm (e.g., the Lipman-Pearson method), to thereby assign maximum homology to conserved amino acid residues present in the amino acid sequences. When the amino acid sequences of the alkaline proteases are aligned through such a method, no matter what insertion or deletion is present in the amino acid sequences, the positions of the homologous amino acid residues in each of the proteases can be determined. Conceivably, the homologous amino acid residues are located at the same positions in the three-dimensional structures of the alkaline proteases, and thus these proteases are analogous in terms of specificity-related functions.

Specifically, an amino acid residue at a corresponding position can be identified as described below on the basis of FIG. 1, in which amino acid sequences are aligned through the aforementioned method.

(1) The amino acid residue at position 132 of the amino acid sequence of SEQ ID NO: 3 is an alanine residue, and, in the case of protease E-1, the amino acid residue at a position corresponding thereto can be identified as an alanine residue at position 131 through the aforementioned method.

(2) The amino acid residue at position 133 of the amino acid sequence of SEQ ID NO: 3 is an alanine residue, and, in the case of protease Ya, the amino acid residue at a position corresponding thereto can be identified as a proline residue at position 132 through the aforementioned method.

(3) The amino acid residue at position 134 of the amino acid sequence of SEQ ID NO: 3 is a valine residue, and, in the case of protease KP9860, the amino acid residue at a position corresponding thereto can be identified as a valine residue at position 134 through the aforementioned method.

(4) The amino acid residue at position 135 of the amino acid sequence of SEQ ID NO: 3 is an asparagine residue, and, in the case of protease SD521, the amino acid residue at a position corresponding thereto can be identified as an asparagine residue at position 134 through the aforementioned method.

Specific positions corresponding to (1) position 132, (2) position 133, (3) position 134, and (4) position 135 of the amino acid sequence of protease KP43, as well as amino acid residues at the respective corresponding positions are shown for the aforementioned protease KP9860, protease E-1, protease Ya, protease SD521, protease A-1, protease A-2, and protease 9865 (Table 1).

TABLE 1

| Position | Proteases | | | | | | | |
| --- | --- | --- | --- | --- | --- | --- | --- | --- |
| | KP43 | KP9860 | E-1 | Ya | SD-521 | A-1 | A-2 | 9865 |
| (1) | Ala 132 | Ala 132 | Ala 131 | Ala 131 | Ala 131 | Ala 132 | Ala 131 | Ala 132 |
| (2) | Ala 133 | Ala 133 | Pro 132 | Pro 132 | Pro 132 | Pro 133 | Pro 132 | Ala 133 |
| (3) | Val 134 | Val 134 | Val 133 | Val 133 | Val 133 | Val 134 | Val 133 | Val 134 |
| (4) | Asn 135 | Asn 135 | Asn 134 | Asn 134 | Asn 134 | Asn 135 | Asn 134 | Asn 135 |

When the alkaline protease of the present invention is a mutant protease, the alkaline protease is obtained through mutation of a target site of a non-mutated alkaline protease (hereinafter may be referred to as a "parent alkaline protease"); i.e., the alkaline protease having the amino acid sequence of SEQ ID NO: 3, or an alkaline protease that is functionally equivalent thereto.

For example, the alkaline protease of the present invention can be obtained by subjecting the amino acid sequence (SEQ ID NO: 3) of protease KP43 to amino acid residue substitution and/or insertion described above in 6) through 16), or by subjecting the amino acid sequence of an alkaline protease that is functionally equivalent to protease KP43 to similar amino acid residue substitution and/or insertion at a position corresponding to the position at which the above substitution and/or insertion is carried out.

The alkaline protease of the present invention can be obtained through, for example, the following procedure. Specifically, a cloned gene encoding a parent alkaline protease (SEQ ID NO: 1) is subjected to mutation; an appropriate host is transformed with the thus-mutated gene; and the thus-transformed host is subjected to culturing, followed by collection of the alkaline protease from the cultured product. Cloning of the gene encoding the parent alkaline protease may be performed through a generally employed genetic recombination technique, for example, a method described in WO99/18218 or WO98/56927.

Mutation of the gene encoding the parent alkaline protease may be performed through any of generally employed site-directed mutagenesis techniques. More specifically, mutation of the gene may be performed by use of, for example, a Site-Directed Mutagenesis System Mutan-Super Express Km kit (Takara). An arbitrary sequence fragment of the gene may be substituted with a sequence fragment of another gene that corresponds to the arbitrary sequence fragment through recombinant PCR (polymerase chain reaction) (PCR protocols, Academic Press, New York, 1990).

The method for producing the protease of the present invention by use of the above-obtained mutant gene is, for example, as follows: a method in which the mutant gene is ligated into a DNA vector which can stably amplify the gene, followed by transformation of a host bacterium; or a method in which the mutant gene is introduced into chromosomal DNA of a host bacterium which can stably maintain the gene. Examples of the host bacterium exhibiting the aforementioned characteristics include bacteria belonging to the genus *Bacillus, Escherichia coli*, mold, yeast, and actinomyces. The protease can be produced by inoculating the host microorganisms containing the mutant gene into a culture medium containing an assimilable carbon source, a nitrogen source, and other essential nutrients, followed by culturing through a customary method.

The thus-produced alkaline protease of the present invention exhibits oxidizer resistance, maintains casein-degrading activity even in the presence of a fatty acid of high concentration, has a molecular weight of 43,000±2,000 as determined by SDS-PAGE, and exhibits activity within an alkaline region. In addition, the alkaline protease is provided with excellent characteristics; i.e., the alkaline protease exhibits a specific activity and/or detergency higher than that of a parent alkaline protease.

Therefore, the alkaline protease of the present invention is useful as an enzyme to be incorporated into a variety of detergent compositions.

No particular limitation is imposed on the amount of the alkaline protease of the present invention to be incorporated into a detergent composition, so long as the protease exhibits its activity. The amount of the alkaline protease to be incorporated may be 0.1 to 5,000 PU on the basis of 1 kg of the detergent composition, but, from the viewpoint of economy, etc., the incorporation amount is preferably 500 PU or less.

The detergent composition of the present invention may contain, in addition to the alkaline protease of the present invention, a variety of enzymes, for example, hydrolase, oxidase, reductase, transferase, lyase, isomerase, ligase, and synthetase. Of these, protease other than the alkaline protease of the present invention, cellulase, keratinase, esterase, cutinase, amylase, lipase, pullulanase, pectinase, mannanase, glucosidase, glucanase, cholesterol oxidase, peroxidase, laccase, and the like are preferred, with protease, cellulase, amylase, and lipase being particularly preferred. Examples of the protease include commercially available products, such as Alcalase, Esperase, Savinase, Everlase, and Kannase (registered trademark; Novozymes); Properase and Purafect (registered trademark; Genencor); and KAP (Kao Corporation). Examples of the cellulase include Celluzyme and Carezyme (registered trademark; Novozymes); and KAC, alkaline cellulase produced by *Bacillus* sp. KSM-S237 strain described in JP-A-10-313859, and mutant alkaline cellulase described in JP-A-2003-313592 (these are products of Kao Corporation). Examples of the amylase include Termamyl, Duramyl, and Stainzyme (registered trademark; Novozymes); Purastar (registered trademark; Genencor), and KAM (Kao Corporation). Examples of the lipase include Lipolase, Lipolase Ultra, and Lipex (registered trademark; Novozymes).

When protease other than the alkaline protease of the present invention is incorporated into a detergent composition in combination with the alkaline protease, the protease content is preferably 0.1 to 500 PU on the basis of 1 kg of the detergent composition. When cellulase is incorporated in combination with the alkaline protease, the cellulase content is preferably 300 to 3,000,000 KU on the basis of 1 kg of the detergent composition, wherein KU represents a unit as determined by the enzyme activity measuring method described in paragraph [0020] of JP-A-10-313859.

When amylase is incorporated in combination with the alkaline protease, the amylase content is preferably 50 to 500,000 IU on the basis of 1 kg of the detergent composition, wherein IU represents a unit as determined by the amylase activity measuring method described in paragraph [0040] of JP-A-11-43690.

When lipase is incorporated in combination with the alkaline protease, the lipase content is preferably 10,000 to 1,000,000 LU on the basis of 1 kg of the detergent composition, wherein LU represents a unit as determined by the lipase activity measuring method described in Example 1 of JP-A-8-500013.

The detergent composition of the present invention may contain a known detergent component, examples of which include the following.

(1) Surfactant

A surfactant is incorporated into the detergent composition in an amount of 0.5 to 60 mass %, preferably 10 to 45 mass % for the case where the detergent composition is in a powder form, and 20 to 50 mass % for the case where the detergent composition is in a liquid form. When the detergent composition of the present invention is employed as a bleaching agent or a detergent for an automatic dishwasher, the amount of a surfactant to be incorporated is generally 1 to 10 mass %, preferably 1 to 5 mass %.

Examples of the surfactant to be employed in the detergent composition of the present invention include one species selected from among an anionic surfactant, a nonionic surfactant, an amphoteric surfactant, and a cationic surfactant; and a combination of these surfactants. Preferably, an anionic surfactant or a nonionic surfactant is employed.

Preferred examples of the anionic surfactant include C10-C18 alcohol sulfuric acid ester salts, C8-C20 alkoxy alcohol sulfuric acid ester salts, alkylbenzenesulfonic acid salts, paraffinsulfonic acid salts, $\alpha$-olefinsulfonic acid salts, $\alpha$-sulfo fatty acid salts, $\alpha$-sulfo fatty acid alkyl ester salts, and fatty acid salts. In the present invention, linear alkylbenzenesulfonic acid salts having a C10-C14 (more preferably C12-C14) alkyl group are preferred. The counter ionic species is preferably an alkali metal ion or an amine ion, preferably a sodium ion and/or a potassium ion; a monoethanolamine ion; or a diethanolamine ion.

Preferred examples of the nonionic surfactant include polyoxyalkylene C8-C20 alkyl ethers, alkyl polyglycosides, polyoxyalkylene C8-C20 alkylphenyl ethers, polyoxyalkylene sorbitan C8-C22 fatty acid esters, polyoxyalkylene glycol C8-C22 fatty acid esters, and polyoxyethylene-polyoxypropylene block polymers. The nonionic surfactant is preferably a polyoxyalkylene alkyl ether obtained through addition of an alkylene oxide such as ethylene oxide or propylene oxide (4 to 20 mol) to a C10-C18 alcohol, the polyoxyalkylene alkyl ether having an HLB value (calculated by the Griffin method) of 10.5 to 15.0, preferably 11.0 to 14.5.

(2) Divalent Metal-Ion Trapping Agent

A divalent metal-ion trapping agent is incorporated in an amount of 0.01 to 50 mass %, preferably 5 to 40 mass %. Examples of the divalent metal-ion trapping agent to be employed in the detergent composition of the present invention include condensed phosphoric acid salts such as tripolyphosphoric acid salts, pyrophosphoric acid salts, and orthophosphoric acid salts; aluminosilicates such as zeolite; synthetic layered crystalline silicic acid salts; nitrilotriacetic acid salts; ethylenediaminetetraacetic acid salts; citric acid salts; isocitric acid salts; and polyacetal carboxylic acid salts. Of these, crystalline aluminosilicates (synthetic zeolite) are preferred. Among A-type, X-type, and P-type zeolites, an A-type zeolite is preferred. The preferably employed synthetic zeolite has an average primary particle size of 0.1 to 10 µm, more preferably 0.1 to 5 µm.

(3) Alkaline Agent

An alkaline agent is incorporated in an amount of 0.01 to 80 mass %, preferably 1 to 40 mass %. Examples of the alkaline agent to be employed in a powder detergent include alkali metal carbonates such as sodium carbonate, which is generally called dense ash or light ash, and amorphous alkali metal silicates of JIS No. 1, 2, or 3. These inorganic alkaline agents are effective in forming particle cores upon drying of a detergent to be able to provide a comparatively hard detergent having excellent fluidity. In place of these alkaline agents, for example, sodium sesquicarbonate or sodium hydrogencarbonate may be used, and a phosphoric acid salt such as a tripolyphosphoric acid salt also acts as an alkaline agent. Examples of the alkaline agent which may be employed in a liquid detergent and act as a counter ion to a surfactant include sodium hydroxide and mono-, di-, or tri-ethanolamine, as well as the aforementioned alkaline agents.

(4) Anti-redeposition Agent

An anti-redeposition agent is incorporated in an amount of 0.001 to 10 mass %, preferably 1 to 5 mass %. Examples of the anti-redeposition agent to be employed in the detergent composition of the present invention include polyethylene glycol, a carboxylic acid polymer, polyvinyl alcohol, and polyvinylpyrrolidone. Of these, a carboxylic acid polymer has metal-ion trapping ability and ability to disperse solid particulate dirt from clothes to a washing bath, as well as anti-redeposition ability. The carboxylic acid polymer is a homopolymer or copolymer formed of acrylic acid, methacrylic acid, itaconic acid, etc., and the copolymer is preferably formed through copolymerization of the aforementioned monomer with maleic acid. The molecular weight of the copolymer is preferably some thousands to 100,000. In addition to the aforementioned carboxylic acid polymer, a polymer such as a polyglycidic acid salt, a cellulose derivative such as carboxymethyl cellulose, or an aminocarboxylic acid polymer such as polyaspartic acid is preferably employed, since these substances also have metal-ion trapping ability, dispersibility, and anti-redeposition ability.

(5) Bleaching Agent

A bleaching agent such as hydrogen peroxide or a percarbonate is preferably incorporated in an amount of 1 to 10 mass %. In the case where a bleaching agent is employed, a bleach-activator such as tetraacetylethylenediamine (TAED) or one described in JP-A-6-316700 may be incorporated in an amount of 0.01 to 10 mass %.

(6) Fluorescent Agent

Examples of the fluorescent agent to be employed in the detergent composition of the present invention include biphenyl fluorescent agents (e.g., Cinopal CBS-X) and stilbene fluorescent agents (e.g., DM-type fluorescent dyes). Such a fluorescent agent is preferably incorporated in an amount of 0.001 to 2 mass %.

(7) Other Components

The detergent composition of the present invention may contain a builder, a softening agent, a reducing agent (e.g., a sulfurous acid salt), a defoaming agent (e.g., silicone), or a perfume, which are known in the laundry detergent field; or other additives.

The detergent composition of the present invention can be produced through a customary method using the above-obtained alkaline protease of the present invention in combination with the aforementioned known detergent components. The form of the detergent may be appropriately determined in accordance with use thereof, and the detergent may assume the form of, for example, liquid, powder, granule, paste, or solid.

The thus-produced detergent composition of the present invention can be employed as, for example, a laundry detergent, a bleaching agent, a detergent for cleaning hard surfaces, a detergent for drainpipes, a denture-cleaning agent, and a detergent for sterilizing medical instruments.

EXAMPLES

Example 1

On the basis of the results of alignment of amino acid sequences (FIG. 1), in a fragment of about 2.0 kb (including a termination codon) of the alkaline protease structural gene (SEQ ID NO: 1) derived from *Bacillus* sp. KSM-KP43 strain, the positions of the amino acid residues to be subjected to site-directed mutation were specified to be 63, 101, and 133. Primers were designed for introducing arbitrary amino acids to these positions. PCR was performed by use of the thus-designed primers; specifically, for mutation introduction at position 63, employed were a primer 1 (SEQ ID NO: 4) and a primer 2 (SEQ ID NO: 5), and a primer 3 (SEQ ID NO: 6) and a primer 4 (SEQ ID NO: 7); for mutation introduction at position 101, employed were the primer 1 and a primer 5 (SEQ ID NO: 8), and a primer 6 (SEQ ID NO: 9) and the primer 4; and for mutation introduction at position 133, employed were the primer 1 and a primer 7 (SEQ ID NO: 10), and a primer 8 (SEQ ID NO: 11) and the primer 4. In the primer 1, a BamHI linker was provided at the 5'-end of the sense strand, and in the primer 4, an XbaI linker was provided at the 5'-end of the antisense strand. The primers 2 and 3 were designed such that they are complementary to each other at sequences of 10 to 15 bp from the respective 5'-ends. In a manner similar to that described above, the primers 5 and 6, and the primers 7 and 8 were designed. Pyrobest (Takara) was employed as DNA polymerase for the PCR. After template DNA was denatured at 94° C. for two minutes, the PCR was performed for 30 cycles, each cycle including 94° C.×one minute, 55° C.×one minute, and 72° C.×one minute. The thus-amplified DNA fragments were purified by use of a PCR product purification kit (Roche). Subsequently, template DNA was denatured at 94° C. for two minutes by use of merely the corresponding amplified fragments, and then recombinant PCR was performed for 30 cycles, each including 94° C.×one minute, 55° C.×one minute, and 72° C.×one minute. PCR was performed on the thus-amplified fragments by use of the primers 1 and 4. After template DNA was denatured at 94° C. for two minutes, the PCR was performed for 30 cycles, each including 94° C.×one minute, 55° C.×one minute, and 72° C.×two minutes, to thereby yield a mutated full-length gene. The thus-amplified fragments were purified, and then the restriction enzyme linkers antached to the termini were cleaved by use of BamHI and XbaI (Roche). The amplified DNA fragments were mixed with plasmid pHA64 (Japanese Patent No. 349293: having BamHI and XbaI cleavage sites downstream of promoter 64) which had been treated in advance with BamHI and XbaI, followed by ligation by use of Ligation High (Toyobo). *Bacillus* sp. KSM-9865 strain (FERM P-18566); i.e., host bacterium, was transformed by use of the plasmid recovered from the resultant reaction mixture through ethanol precipitation.

The thus-transformed strain 9865 was grown in a skim milk-containing alkaline agar medium [1% (w/v) skim milk (Difco), 1% bactotryptone (Difco), 0.5% yeast extract (Difco), 1% sodium chloride, 1.5% agar, 0.05% sodium carbonate, and 15 ppm tetracycline], and introduction of the mutant protease gene was determined on the basis of the state of halo formation. The transformant was inoculated into a seed culture medium (5 mL) [6.0% (w/v) polypeptone S, 0.05% yeast extract, 1.0% maltose, 0.02% magnesium sulfate heptahydrate, 0.1% potassium dihydrogenphosphate, 0.25% sodium carbonate, and 30 ppm tetracycline], followed by shaking culture at 30° C. for 16 hours. Subsequently, the resultant seed culture broth (1% (v/v)) was inoculated into a primary culture medium (30 mL) [8% polypeptone S, 0.3% yeast extract, 10% maltose, 0.04% magnesium sulfate heptahydrate, 0.2% potassium dihydrogenphosphate, 1.5% anhydrous sodium carbonate, and 30 ppm tetracycline], followed by shaking culture at 30° C. for three days.

The resultant culture broth was subjected to centrifugation, and the protease activity of the resultant culture supernatant was measured. The protease activity was measured through an activity measuring method employing, as a substrate, Suc-Ala-Ala-Pro-Phe-pNA (hereinafter will be abbreviated as "AAPF": Sigma), and the amount of the resultant protein was measured by use of a protein assay kit (Wako Pure Chemical Industries, Ltd.). The protease activity of the culture supernatant was compared with that of a culture supernatant obtained through culturing of a transformant containing a wild-type protease gene under the same conditions as described above, whereby a mutant protease gene exhibiting enhanced protease activity was selected.

The plasmid was recovered from the selected transformant by use of a High pure plasmid isolation kit (Roche), and then subjected to sequencing. Specifically, PCR was performed by use of plasmid DNA (300 ng) serving as a template, an appropriately synthesized primer, and a Big Dye DNA sequencing kit (Applied Biosystems) (reaction system: 20 µL), followed by analysis employing a DNA Sequencer (model: 377, Applied Biosystems).

As a result, in a mutant protease exhibiting enhanced protease activity, alanine at position 133 was found to be substituted with glutamine, asparagine, threonine, valine, isoleucine, leucine, or lysine. An aliquot of a culture broth containing such a mutant protease was diluted, and the thus-diluted broth was applied to a DEAE-Toyopearl (Tosoh Corporation) column equilibrated with a 10 mM Tris-HCl buffer (pH 7.5) containing 2 mM calcium chloride, followed by recovery of non-adsorbed fractions, to thereby yield an almost uniform protease. The protein content of the thus-purified enzyme and the AAPF degradation activity of the enzyme were measured, and as a result, the specific activity of the enzyme was found to be increased by a factor of 1.2 to 2 through introduction of the above-described mutation (Table 2).

TABLE 2

| Mutated site sequence | Protease relative specific activity (%) |
|---|---|
| Wild type | 100 |
| *A133Q | 121.7 |
| A133N | 136.8 |
| A133T | 139.9 |
| A133V | 153.9 |
| A133I | 160.2 |
| A133L | 197.0 |
| A133K | 217.0 |

Figure 3:
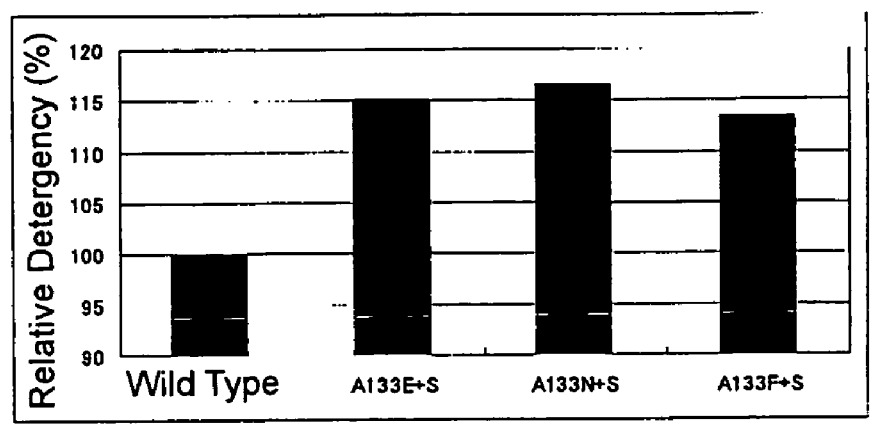
Figure 4:
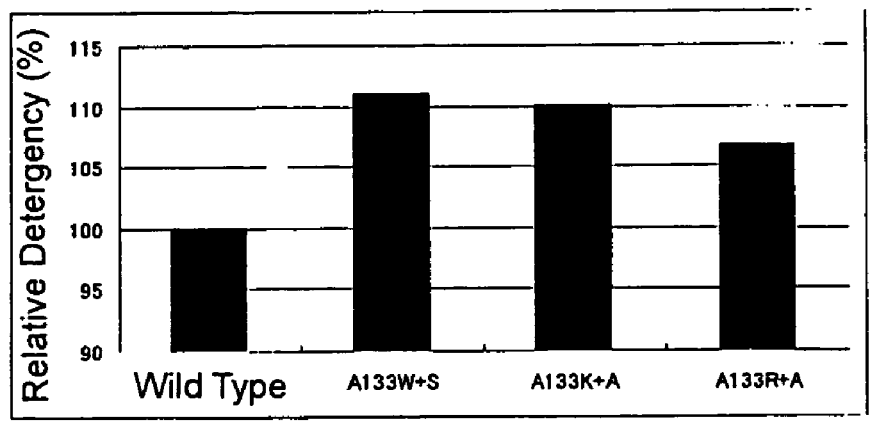

In Table 2, an amino acid is represented by one letter of the alphabet, and the position at which amino acid substitution occurs is represented by a numeral. The letter preceding the numeral and the letter subsequent to the numeral represent the amino acid before substitution and the amino acid after substitution, respectively. For example, "A133Q" represents a mutant protease obtained through substitution of alanine at position 133 with glutamine. This representation will also be applied to Table 3 and FIGS. 2-1 through 2-6.

Subsequently, in order to provide the position 133 mutation with diversity, the following mutation was introduced:

(1) insertion of one arbitrary amino acid between positions 133 and 134;

(2) substitution with an arbitrary amino acid at position 133, and insertion of one arbitrary amino acid;

(3) substitution with an arbitrary amino acid at position 133, insertion of one arbitrary amino acid, and substitution with an arbitrary amino acid at position 134;

(4) substitution with an arbitrary amino acid at position 133, insertion of one arbitrary amino acid, and substitution with arbitrary amino acids at positions 134 and 135;

(5) substitution with an arbitrary amino acid at position 132, and insertion of one arbitrary amino acid between positions 133 and 134; or (6) substitution with arbitrary amino acids at positions 132 and 133, and insertion of one arbitrary amino acid.

Recombinant PCR was performed as described above by use of the following primers; i.e., the primer 1, the primer 7, a primer 9 (SEQ ID NO: 12), and the primer 4 for the mutation introduction (1); the primer 1, the primer 7, a primer 10 (SEQ ID NO: 13), and the primer 4 for the mutation introduction (2); the primer 1, the primer 7, a primer 11 (SEQ ID NO: 14), and the primer 4 for the mutation introduction (3); the primer 1, the primer 7, a primer 12 (SEQ ID NO: 15), and the primer 4 for the mutation introduction (4); the primer 1, a primer 13 (SEQ ID NO: 16), a primer 14 (SEQ ID NO: 17), and the primer 4 for the mutation introduction (5); or the primer 1, the primer 7, a primer 15 (SEQ ID NO: 18), and the primer 4 for the mutation introduction (6), to thereby yield a mutated gene. The gene was ligated to the aforementioned pHA64, and subsequently the strain 9865 was transformed, followed by culturing. The thus-produced mutant protease was evaluated in terms of protease activity.

As a result, the following mutant proteases were found to exhibit a protease activity higher than that of the wild-type protease:

a mutant protease obtained through the mutation (1)

amino acid residue inserted between positions 133 and 134: lysine or tyrosine;

a mutant protease obtained through the mutation (2)

amino acid residue substituted at position 133+inserted amino acid residue: proline+isoleucine, leucine+serine, leucine+glycine, leucine+threonine, serine+serine, lysine+serine, isoleucine+serine, arginine+serine, lysine+alanine, or lysine+glycine;

a mutant protease obtained through the mutation (3)

amino acid residue substituted at position 133+inserted amino acid residue/amino acid residue substituted at position 134: serine+serine/threonine, serine+serine/serine, serine+serine/glycine, or serine+serine/alanine;

a mutant protease obtained through the mutation (4)

amino acid residue substituted at position 133+inserted amino acid residue/amino acid residue substituted at position 134/amino acid residue substituted at position 135: serine+serine/serine/alanine, serine+serine/serine/arginine, or serine+serine/serine/methionine;

a mutant protease obtained through the mutation (5)

amino acid residue substituted at position 132/amino acid residue inserted between positions 133 and 134: serine/alanine, serine/glycine, methionine/alanine, or threonine/alanine; and a mutant protease obtained through the mutation (6)

amino acid residue substituted at position 132/amino acid residue substituted at position 133+inserted amino acid residue: serine/serine+serine, glutamine/serine+serine, methionine/serine+serine, serine/isoleucine+alanine, serine/lysine+alanine, serine/lysine+serine, asparagine/proline+alanine, aspartic acid/lysine+serine, or isoleucine/lysine+serine.

These mutant proteases were subjected to measurement of specific activity through the above-described method, and were found to exhibit a specific activity 1.2 to 4.8 times that of the wild-type protease (Table 3).

TABLE 3

| | Protease relative specific activity (%) |
|---|---|
| Wild type | 100 |
| *A133P + I | 156.3 |
| A133L + T | 198.9 |
| A133L + S | 243.3 |
| A133L + G | 263.7 |
| A133S + S | 122.4 |
| +K | 141.4 |
| +Y | 138.5 |
| A133K + S | 125.2 |
| A133I + S | 167.8 |
| A133R + S | 142.0 |
| A133K + A | 142.8 |
| A133K + G | 135.3 |
| A133S + S/V134G | 125.0 |
| A133S + S/V134T | 173.3 |
| A133S + S/V134A | 207.2 |
| A133S + S/V134S | 216.2 |
| A133S + S/V134S/N135A | 190.7 |
| A133S + S/V134S/N135R | 221.2 |
| A133S + S/V134S/N135M | 231.5 |
| A132Q/A133S + S | 153.9 |
| A132S/A133S + S | 134.1 |
| A132M/A133S + S | 224.3 |
| A132S/A133I + A | 263.7 |
| A132S/+A | 126.4 |
| A132S/+G | 141.6 |
| A132S/A133K + A | 171.8 |
| A132S/A133K + S | 179.2 |
| A132N/A133P + A | 486.4 |
| A132M/+A | 253.2 |
| A132T/+A | 132.8 |
| A132D/A133K + S | 148.2 |
| A132I/A133K + S | 228.0 |

In Table 3, an amino acid inserted between positions 133 and 134 is represented by use of "+." For example, "A133P+I" represents a mutant protease obtained through substitution of alanine at position 133 with proline and insertion of isoleucine, and "+K" represents a mutant protease obtained through insertion of lysine between positions 133 and 134. This representation will also be applied to FIGS. 2-1 through 2-6.

The thus-obtained mutant proteases were evaluated in terms of detergency, and, for example, mutant proteases containing amino acid residues modified as described below were found to exhibit a detergency higher than that of the wild-type protease (FIGS. 2-1 through 2-6):

(1) amino acid residue substituted at position 133: isoleucine or valine;

(2) amino acid residue inserted between positions 133 and 134: lysine, leucine, serine, methionine, glycine, threonine, tyrosine, or arginine;

(3) amino acid residue substituted at position 133+inserted amino acid residue: serine+serine, serine+alanine, serine+asparagine, serine+glutamine, serine+tryptophan, serine+histidine, serine+glycine, leucine+serine, lysine+serine, threonine+serine, isoleucine+serine, methionine+serine, glycine+serine, arginine+serine, glutamic acid+serine, asparagine+serine, phenylalanine+serine, tryptophan+serine, lysine+alanine, arginine+alanine, or lysine+glycine;

(4) amino acid residue substituted at position 133+inserted amino acid residue/amino acid residue substituted at position 134: serine+serine/serine or serine+serine/threonine;

(5) amino acid residue substituted at position 133+inserted amino acid residue/amino acid residue substituted at position 134/amino acid residue substituted at position 135: serine+serine/serine/methionine;

(6) amino acid residue substituted at position 132/amino acid residue inserted between positions 133 and 134: serine/alanine, serine/arginine, serine/glycine, serine/leucine, or threonine/alanine; and (7) amino acid residue substituted at position 132/amino acid residue substituted at position 133+inserted amino acid residue: serine/histidine+alanine, serine/serine+alanine, serine/leucine+alanine, serine/arginine+alanine, serine/lysine+alanine, serine/lysine+serine, asparagine/isoleucine+alanine, asparagine/proline+alanine, or aspartic acid/lysine+serine.

In order to evaluate thermal resistance of the mutant proteases, each of the mutant proteases was thermally treated in 2 mM aqueous calcium chloride solution at 75° C. for 10 minutes; the AAPF degradation activity of thus-treated protease was measured; and the residual activity thereof was calculated on the basis of that of a non-treated enzyme sample (taken as 100%). As a result, the mutant protease in which the amino acid residue substituted at position 133 and the inserted amino acid residue are serine and serine, respectively, was found to exhibit a residual activity of 76%, which is about 1.5 times that of the wild-type protease (i.e., 50%).

The aforementioned mutant alkaline proteases of the present invention were found to exhibit enhanced AAPF degradation activity, and enhanced detergency (among them, the mutant protease in which the amino acid residue substituted at position 133 and the inserted amino acid residue are serine and serine, respectively, further exhibited enhanced thermal resistance). In addition, the alkaline proteases were found to exhibit the characteristics of the parental alkaline protease; i.e., exhibiting oxidizer resistance, maintaining casein-degrading activity even in the presence of a fatty acid of high concentration, having a molecular weight of 43,000±2,000 as determined by SDS-PAGE, and exhibiting activity within an alkaline region.

Test Example 1

Protease Activity Measuring Method (Synthetic Substrate Method)

100 mM AAPF (dissolved in DMSO, final concentration: 3 mM), a 0.2 M borate buffer (pH 10.5, final concentration: 50 mM), and an appropriately diluted culture supernatant (50 μL) were added to a microplate (volume adjusted to 100 μL). Thereafter, absorbance at 414 nm was measured in a time-course manner by use of a microplate reader (iEMS Reader MF, product of Labsystems) under shaking at 30° C. for 15 minutes, and a change in absorbance per unit time (OD414/min) was obtained. The thus-obtained gradient was multiplied by the percent dilution of enzyme, and the thus-calculated value (i.e., protease titer) was employed for comparative evaluation of the mutant proteases.

Test Example 2

Protease Activity Measuring Method (Casein Method)

A 50 mM borate buffer (pH 10.5) (1 mL) containing 1% (w/v) casein (the Hammerstein method: Merck) was maintained at 30° C. for five minutes, and subsequently an enzyme liquid (0.1 mL) was added to the buffer, to thereby allow reaction to proceed for 15 minutes. Thereafter, a reaction stopping solution (0.11 M trichloroacetic acid/0.22 M sodium acetate/0.33 M acetic acid) (2 mL) was added to the resultant reaction mixture. The mixture was allowed to stand at room temperature for 30 minutes, and the resultant mixture containing precipitates was subjected to filtration by use of Whatman filter paper No. 1. The amount of the degradation product was determined through the method of Lowry, et al. Specifically, an alkaline copper solution (1% Rochelle salt 1% copper sulfate pentahydrate:2% sodium carbonate/0.1 N sodium hydroxide solution=1:1:100)(2.5 mL) was added to the above-obtained filtrate (0.5 mL), and the resultant mixture was maintained at 30° C. for 10 minutes. Subsequently, to the mixture was added a phenol reagent [a solution obtained by diluting a commercially available phenol reagent (Kanto Kagaku) two-fold with deionized water] (0.25 mL), and the resultant mixture was well stirred and then allowed to stand at 30° C. for 30 minutes. Thereafter, the absorbance of the mixture was measured at 660 nm. One unit of protease activity (1 PU) was defined as the amount of the enzyme required for producing acid-soluble proteins equivalent to 1 mmol of tyrosine per minute under the above reaction conditions.

Test Example 3

Relative Detergency

Detergency of the mutant enzyme was evaluated by use of a Terg-O-Tometer (Ueshima Seisakusho Co., Ltd.). Enzyme granules were removed from a commercially available laundry detergent (Attack, produced by Kao Corporation in October 2002); a solution of the resultant detergent was prepared such that the detergent concentration became a predetermined level; and the mutant enzyme was added to the solution such that the final concentration of the enzyme became 40 mPU/L. Subsequently, five of cut pieces (6 cm×6 cm) of dirty fabric EMPA 117 (product of EMPA, blood/milk/carbon) were added to the above-prepared solution, and unless othertion at 20° C. (80 rpm), followed by rinsing with tap water. Thereafter, the brightness of the fabric pieces were measured by use of a spectrophotometer (CM3500d, product of MINOLTA), and the detergency was calculated on the basis of the brightnesses of the fabric piece before and after washing by use of the following formula.

Detergency (%)=(L2−L1)/(L0−L1)×100

L0: brightness of original fabric
L1: brightness of dirty fabric before washing
L2: brightness of dirty fabric after washing The relative detergency of the mutant enzyme was obtained on the basis of the detergency of the wild-type enzyme (taken as 100).

---

We claim:

1. An isolated protein comprising the polypeptide of SEQ ID NO: 3, or polypeptide that is at least 95% identical to SEQ ID NO: 3, wherein the polypeptide comprises at least one modification (a) through (e), and wherein the polypeptide exhibits an alkaline protease activity and/or detergency higher than that of the alkaline protease of SEQ ID NO: 3:
   (a) substitution, with an amino acid residue selected from the group consisting of lysine, threonine, asparagine, glutamine, valine, leucine, or isoleucine, of the amino acid residue at position 133 or at a position corresponding thereto;
   (b) insertion of an amino acid residue between the amino acid residues at positions 133 and 134 or at positions corresponding thereto;
   (c) substitution, with an amino acid residue, of the amino acid residue at original position 134 (as used herein, the "original position" refers to the position before insertion) or at a position corresponding thereto;
   (d) substitution, with an amino acid residue, of the amino acid residue at original position 135 or at a position corresponding thereto; and
   (e) substitution, with an amino acid residue, of the amino acid residue at position 132 or at a position corresponding thereto.

2. An isolated protein comprising the polypeptide of SEQ ID NO: 3, or a polypeptide that is at least 95% identical to SEQ ID NO: 3, wherein the polypeptide comprises at least one modification (a) through (e), and which exhibits an alkaline protease activity and/or detergency higher than that of the alkaline protease of SEQ ID NO: 3:
   (a) substitution, with an amino acid residue, of the amino acid residue at position 133 or at a position corresponding thereto;
   (b) insertion of an amino acid residue between the amino acid residues at positions 133 and 134 or at positions corresponding thereto;
   (c) substitution, with an amino acid residue, of the amino acid residue at original position 134 (as used herein, the "original position" refers to the position before insertion) or at a position corresponding thereto;
   (d) substitution, with an amino acid residue, of the amino acid residue at original position 135 or at a position corresponding thereto; and
   (e) substitution, with an amino acid residue, of the amino acid residue at position 132 or at a position corresponding thereto,
   wherein the amino acid residue substitution and/or insertion is selected from the group consisting of:
   1) combination of the amino acid residue substitution of modification (a) and the amino acid residue insertion of modification (b);
   2) combination of the amino acid residue substitution of modification (a), the amino acid residue insertion of modification (b), and the amino acid residue substitution of modification (c);
   3) combination of the amino acid residue substitution of modification (a), the amino acid residue insertion of modification (b), the amino acid residue substitution of modification (c), and the amino acid residue substitution of modification (d);
   4) combination of the amino acid residue substitution of modification (a), the amino acid residue insertion of modification of (b), and the amino acid residue substitution of modification of (e); and
   5) combination of the amino acid residue insertion of modification (b) and the amino acid residue substitution of modification (e).

3. An isolated protein comprising the polypeptide of SEQ ID NO: 3, or a polypeptide that is at least 95% identical to SEQ ID NO: 3, wherein the polypeptide comprises at least one modification (a) through (e), and which exhibits an alkaline protease activity and/or detergency higher than that of the alkaline protease of SEQ ID NO: 3:
   (a) substitution, with an amino acid residue, of the amino acid residue at position 133 or at a position corresponding thereto;
   (b) insertion of an amino acid residue between the amino acid residues at positions 133 and 134 or at positions corresponding thereto;
   (c) substitution, with an amino acid residue, of the amino acid residue at original position 134 (as used herein, the "original position" refers to the position before insertion) or at a position corresponding thereto;
   (d) substitution, with an amino acid residue, of the amino acid residue at original position 135 or at a position corresponding thereto; and
   (e) substitution, with an amino acid residue, of the amino acid residue at position 132 or at a position corresponding thereto,
   wherein the amino acid residue substitution and/or insertion is selected from the group consisting of:
   6) an alkaline protease obtained through the amino acid residue substitution of modification (a), in which the introduced amino acid residue by way of substitution may be lysine, threonine, asparagine, glutamine, valine, leucine, or isoleucine;
   7) an alkaline protease obtained through the amino acid residue insertion of modification (b), in which the inserted amino acid residue may be lysine, leucine, serine, methionine, glycine, threonine, tyrosine, or arginine;
   8) an alkaline protease obtained through combination of the amino acid residue substitution of modification (a) and the amino acid residue insertion of modification (b), in which (a) introduced amino acid residue/(b) inserted amino acid residue may be (a) proline/(b) isoleucine, (a) leucine/(b) serine, (a) leucine/(b) glycine, (a) leucine/(b) threonine, (a) serine/(b) alanine, (a) serine/(b) asparagine, (a) serine/(b) glutamine, (a) serine/(b) tryptophan, (a) serine/(b) histidine, (a) serine/(b) glycine, (a) lysine/(b) serine, (a) threonine/(b) serine, (a) isoleucine/(b) serine, (a) methionine/(b) serine, (a) glycine/(b) serine, (a) arginine/(b) serine, (a) glutamic acid/(b) serine, (a) asparagine/(b) serine, (a) phenylalanine/(b) serine, (a) tryptophan/(b) serine, (a) lysine/(b) alanine, (a) arginine/(b) alanine, (a) lysine/(b) glycine, or (a) serine/(b) serine;

9) an alkaline protease obtained through combination of the amino acid residue substitution of modification (a), the amino acid residue insertion of modification (b), and the amino acid residue substitution of modification (c), in which (a) introduced amino acid residue/(b) inserted amino acid residue/(c) introduced amino acid residue may be (a) serine/(b) serine/(c) threonine, serine, glycine, or alanine;

10) an alkaline protease obtained through combination of the amino acid residue substitution of modification (a), the amino acid residue insertion of modification (b), the amino acid residue substitution of modification (c), and the amino acid residue substitution of modification (d), in which (a) introduced amino acid residue/(b) inserted amino acid residue/(c) introduced amino acid residue/(d) introduced amino acid residue may be (a) serine/(b) serine/(c) serine/(d) alanine, (a) serine/(b) serine/(c) serine/(d) arginine, or (a) serine/(b) serine/(c) serine/(d) methionine;

11) an alkaline protease obtained through combination of the amino acid residue substitution of modification (a), the amino acid residue insertion of modification (b), and the amino acid residue substitution of modification (e), in which (a) introduced amino acid residue/(b) inserted amino acid residue/(e) introduced amino acid residue may be (a) serine/(b) serine/(e) serine, (a) serine/(b) serine/(e) glutamine, or (a) serine/(b) serine/(e) methionine;

12) an alkaline protease obtained through combination of the amino acid residue insertion of modification (b) and the amino acid residue substitution of modification (e), in which (b) inserted amino acid residue/(e) introduced amino acid residue may be (b) alanine, arginine, glycine, or leucine/(e) serine;

13) an alkaline protease obtained through combination of the amino acid residue substitution of modification (a), the amino acid residue insertion of modification (b), and the amino acid residue substitution of modification (e), in which (a) introduced amino acid residue/(b) inserted amino acid residue/(e) introduced amino acid residue may be (a) isoleucine/(b) alanine/(e) serine, (a) histidine/(b) alanine/(e) serine, (a) serine/(b) alanine/(e) serine, (a) leucine/(b) alanine/(e) serine, (a) arginine/(b) alanine/(e) serine, (a) lysine/(b) alanine/(e) serine, or (a) lysine/(b) serine/(e) serine;

14) an alkaline protease obtained through combination of the amino acid residue substitution of modification (a), the amino acid residue insertion of modification (b), and the amino acid residue substitution of modification (e), in which (a) introduced amino acid residue/(b) inserted amino acid residue/(e) introduced amino acid residue may be (a) isoleucine/(b) alanine/(e) asparagine or (a) proline/(b) alanine/(e) asparagine;

15) an alkaline protease obtained through combination of the amino acid residue insertion of modification (b) and the amino acid residue substitution of modification (e), in which (b) inserted amino acid residue/(e) introduced amino acid residue may be (b) alanine/(e) methionine or threonine; and 16) an alkaline protease obtained through combination of the amino acid residue substitution of modification (a), the amino acid residue insertion of modification (b), and the amino acid residue substitution of modification (e), in which (a) introduced amino acid residue/(b) inserted amino acid residue/(e) introduced amino acid residue may be (a) lysine/(b) serine/(e) asparagine or isoleucine.

4. The protein of claim 1, wherein the polypeptide has an amino acid sequence that is at least 95% identical to SEQ ID NO: 3, comprises at least one modification (a) through (e), and has a deletion, substitution, or addition of one to several amino acid residues at positions other than position 132, 133, 134, or 135 of the amino acid sequence of SEQ ID NO: 3 or a position corresponding thereto.

5. A detergent composition comprising the protein of claim 1.

6. The protein of claim 1, wherein the polypeptide has the amino acid sequence corresponding to SEQ ID NO: 3 which comprises at least one modification (a) through (e).

* * * * *

SEQUENCE LISTING

<160> NUMBER OF SEQ ID NOS: 25

<210> SEQ ID NO 1
<211> LENGTH: 1923
<212> TYPE: DNA
<213> ORGANISM: Bacillus sp. KSM-KP43
<220> FEATURE:
<221> NAME/KEY: CDS
<222> LOCATION: (1)..(1920)
<220> FEATURE:
<221> NAME/KEY: sig_peptide
<222> LOCATION: (1)..(618)
<220> FEATURE:
<221> NAME/KEY: mat_peptide
<222> LOCATION: (619)..(1920)

<400> SEQUENCE: 1

```
atg aga aag aag aaa aag gtg ttt tta tct gtt tta tca gct gca         45
Met Arg Lys Lys Lys Lys Val Phe Leu Ser Val Leu Ser Ala Ala
    -205                -200                -195 gcg att ttg tcg act gtt gcg tta agt aat cca tct gca ggt ggt         90
Ala Ile Leu Ser Thr Val Ala Leu Ser Asn Pro Ser Ala Gly Gly
    -190                -185                -180 gca agg aat ttt gat ctg gat ttc aaa gga att cag aca aca act        135
Ala Arg Asn Phe Asp Leu Asp Phe Lys Gly Ile Gln Thr Thr Thr
    -175                -170                -165 gat gct aaa ggt ttc tcc aag cag ggg cag act ggt gct gct gct        180
Asp Ala Lys Gly Phe Ser Lys Gln Gly Gln Thr Gly Ala Ala Ala
    -160                -155                -150 ttt ctg gtg gaa tct gaa aat gtg aaa ctc cca aaa ggt ttg cag        225
Phe Leu Val Glu Ser Glu Asn Val Lys Leu Pro Lys Gly Leu Gln
    -145                -140                -135 aag aag ctt gaa aca gtc ccg gca aat aat aaa ctc cat att atc        270
Lys Lys Leu Glu Thr Val Pro Ala Asn Asn Lys Leu His Ile Ile
    -130                -125                -120 caa ttc aat gga cca att tta gaa gaa aca aaa cag cag ctg gaa        315
Gln Phe Asn Gly Pro Ile Leu Glu Glu Thr Lys Gln Gln Leu Glu
    -115                -110                -105 aaa aca ggg gca aag att ctc gac tac ata cct gat tat gct tac att   363
Lys Thr Gly Ala Lys Ile Leu Asp Tyr Ile Pro Asp Tyr Ala Tyr Ile
    -100                -95                 -90 gtc gag tat gag ggc gat gtt aag tca gca aca agc acc att gag cac   411
Val Glu Tyr Glu Gly Asp Val Lys Ser Ala Thr Ser Thr Ile Glu His
-85                 -80                 -75                 -70 gtg gaa tcc gtg gag cct tat ttg ccg ata tac aga ata gat ccc cag   459
Val Glu Ser Val Glu Pro Tyr Leu Pro Ile Tyr Arg Ile Asp Pro Gln
                    -65                 -60                 -55 ctt ttc aca aaa ggg gca tca gag ctt gta aaa gca gtg gcg ctt gat   507
Leu Phe Thr Lys Gly Ala Ser Glu Leu Val Lys Ala Val Ala Leu Asp
                    -50                 -45                 -40 aca aag cag aaa aat aaa gag gtg caa tta aga ggc atc gaa caa atc   555
Thr Lys Gln Lys Asn Lys Glu Val Gln Leu Arg Gly Ile Glu Gln Ile
            -35                 -30                 -25
```

-continued

| | | |
|---|---|---|
| gca caa ttc gca ata agc aat gat gtg cta tat att acg gca aag cct<br>Ala Gln Phe Ala Ile Ser Asn Asp Val Leu Tyr Ile Thr Ala Lys Pro<br>   -20              -15               -10 | 603 | |
| gag tat aag gtg atg aat gat gtt gcg cgt gga att gtc aaa gcg gat<br>Glu Tyr Lys Val Met Asn Asp Val Ala Arg Gly Ile Val Lys Ala Asp<br>-5               -1  1              5                   10 | 651 | |
| gtg gct cag agc agc tac ggg ttg tat gga caa gga cag atc gta gcg<br>Val Ala Gln Ser Ser Tyr Gly Leu Tyr Gly Gln Gly Gln Ile Val Ala<br>              15                20                25 | 699 | |
| gtt gcc gat aca ggg ctt gat aca ggt cgc aat gac agt tcg atg cat<br>Val Ala Asp Thr Gly Leu Asp Thr Gly Arg Asn Asp Ser Ser Met His<br>         30                35                40 | 747 | |
| gaa gcc ttc cgc ggg aaa att act gca tta tat gca ttg gga cgg acg<br>Glu Ala Phe Arg Gly Lys Ile Thr Ala Leu Tyr Ala Leu Gly Arg Thr<br>    45                50               55 | 795 | |
| aat aat gcc aat gat acg aat ggt cat ggt acg cat gtg gct ggc tcc<br>Asn Asn Ala Asn Asp Thr Asn Gly His Gly Thr His Val Ala Gly Ser<br>60                65                 70              75 | 843 | |
| gta tta gga aac ggc tcc act aat aaa gga atg gcg cct cag gcg aat<br>Val Leu Gly Asn Gly Ser Thr Asn Lys Gly Met Ala Pro Gln Ala Asn<br>              80                85                90 | 891 | |
| cta gtc ttc caa tct atc atg gat agc ggt ggg gga ctt gga gga cta<br>Leu Val Phe Gln Ser Ile Met Asp Ser Gly Gly Gly Leu Gly Gly Leu<br>         95                100              105 | 939 | |
| cct tcg aat ctg caa acc tta ttc agc caa gca tac agt gct ggt gcc<br>Pro Ser Asn Leu Gln Thr Leu Phe Ser Gln Ala Tyr Ser Ala Gly Ala<br>    110               115              120 | 987 | |
| aga att cat aca aac tcc tgg gga gca gca gtg aat ggg gct tac aca<br>Arg Ile His Thr Asn Ser Trp Gly Ala Ala Val Asn Gly Ala Tyr Thr<br>125              130              135 | 1035 | |
| aca gat tcc aga aat gtg gat gac tat gtg cgc aaa aat gat atg acg<br>Thr Asp Ser Arg Asn Val Asp Asp Tyr Val Arg Lys Asn Asp Met Thr<br>140              145              150              155 | 1083 | |
| atc ctt ttc gct gcc ggg aat gaa gga ccg aac ggc gga acc atc agt<br>Ile Leu Phe Ala Ala Gly Asn Glu Gly Pro Asn Gly Gly Thr Ile Ser<br>              160              165              170 | 1131 | |
| gca cca ggc aca gct aaa aat gca ata aca gtc gga gct acg gaa aac<br>Ala Pro Gly Thr Ala Lys Asn Ala Ile Thr Val Gly Ala Thr Glu Asn<br>         175              180              185 | 1179 | |
| ctc cgc cca agc ttt ggg tct tat gcg gac aat atc aac cat gtg gca<br>Leu Arg Pro Ser Phe Gly Ser Tyr Ala Asp Asn Ile Asn His Val Ala<br>    190              195              200 | 1227 | |
| cag ttc tct tca cgt gga ccg aca aag gat gga cgg atc aaa ccg gat<br>Gln Phe Ser Ser Arg Gly Pro Thr Lys Asp Gly Arg Ile Lys Pro Asp<br>205              210              215 | 1275 | |
| gtc atg gca ccg gga acg ttc ata cta tca gca aga tct tct ctt gca<br>Val Met Ala Pro Gly Thr Phe Ile Leu Ser Ala Arg Ser Ser Leu Ala<br>220              225              230              235 | 1323 | |
| ccg gat tcc tcc ttc tgg gcg aac cat gac agt aaa tat gca tac atg<br>Pro Asp Ser Ser Phe Trp Ala Asn His Asp Ser Lys Tyr Ala Tyr Met<br>              240              245              250 | 1371 | |
| ggt gga acg tcc atg gct aca ccg atc gtt gct gga aac gtg gca cag<br>Gly Gly Thr Ser Met Ala Thr Pro Ile Val Ala Gly Asn Val Ala Gln<br>         255              260              265 | 1419 | |
| ctt cgt gag cat ttt gtg aaa aac aga ggc atc aca cca aag cct tct<br>Leu Arg Glu His Phe Val Lys Asn Arg Gly Ile Thr Pro Lys Pro Ser<br>    270              275              280 | 1467 | |
| cta tta aaa gcg gca ctg att gcc ggt gca gct gac atc ggc ctt ggc<br>Leu Leu Lys Ala Ala Leu Ile Ala Gly Ala Ala Asp Ile Gly Leu Gly<br>285              290              295 | 1515 | |

-continued

| | |
|---|---|
| tac ccg aac ggt aac caa gga tgg gga cga gtg aca ttg gat aaa tcc<br>Tyr Pro Asn Gly Asn Gln Gly Trp Gly Arg Val Thr Leu Asp Lys Ser<br>300                   305                   310                   315 | 1563 |
| ctg aac gtt gcc tat gtg aac gag tcc agt tct cta tcc acc agc caa<br>Leu Asn Val Ala Tyr Val Asn Glu Ser Ser Ser Leu Ser Thr Ser Gln<br>                   320                   325                   330 | 1611 |
| aaa gcg acg tac tcg ttt act gct act gcc ggc aag cct ttg aaa atc<br>Lys Ala Thr Tyr Ser Phe Thr Ala Thr Ala Gly Lys Pro Leu Lys Ile<br>               335                   340                   345 | 1659 |
| tcc ctg gta tgg tct gat gcc cct gcg agc aca act gct tcc gta acg<br>Ser Leu Val Trp Ser Asp Ala Pro Ala Ser Thr Thr Ala Ser Val Thr<br>                   350                   355                   360 | 1707 |
| ctt gtc aat gat ctg gac ctt gtc att acc gct cca aat ggc aca cag<br>Leu Val Asn Asp Leu Asp Leu Val Ile Thr Ala Pro Asn Gly Thr Gln<br>365                   370                   375 | 1755 |
| tat gta gga aat gac ttt act tcg cca tac aat gat aac tgg gat ggc<br>Tyr Val Gly Asn Asp Phe Thr Ser Pro Tyr Asn Asp Asn Trp Asp Gly<br>380                   385                   390                   395 | 1803 |
| cgc aat aac gta gaa aat gta ttt att aat gca cca caa agc ggg acg<br>Arg Asn Asn Val Glu Asn Val Phe Ile Asn Ala Pro Gln Ser Gly Thr<br>                   400                   405                   410 | 1851 |
| tat aca att gag gta cag gct tat aac gta ccg gtt gga cca cag acc<br>Tyr Thr Ile Glu Val Gln Ala Tyr Asn Val Pro Val Gly Pro Gln Thr<br>               415                   420                   425 | 1899 |
| ttc tcg ttg gca att gtg aat taa<br>Phe Ser Leu Ala Ile Val Asn<br>               430 | 1923 |

<210> SEQ ID NO 2
<211> LENGTH: 640
<212> TYPE: PRT
<213> ORGANISM: Bacillus sp. KSM-KP43

<400> SEQUENCE: 2

Met Arg Lys Lys Lys Lys Val Phe Leu Ser Val Leu Ser Ala Ala
    -205                      -200                  -195

Ala Ile Leu Ser Thr Val Ala Leu Ser Asn Pro Ser Ala Gly Gly
    -190                      -185                  -180

Ala Arg Asn Phe Asp Leu Asp Phe Lys Gly Ile Gln Thr Thr Thr
    -175                      -170                  -165

Asp Ala Lys Gly Phe Ser Lys Gln Gly Gln Thr Gly Ala Ala Ala
    -160                      -155                  -150

Phe Leu Val Glu Ser Glu Asn Val Lys Leu Pro Lys Gly Leu Gln
    -145                      -140                  -135

Lys Lys Leu Glu Thr Val Pro Ala Asn Asn Lys Leu His Ile Ile
    -130                      -125                  -120

Gln Phe Asn Gly Pro Ile Leu Glu Glu Thr Lys Gln Gln Leu Glu
    -115                      -110                  -105

Lys Thr Gly Ala Lys Ile Leu Asp Tyr Ile Pro Asp Tyr Ala Tyr Ile
    -100                     -95                   -90

Val Glu Tyr Glu Gly Asp Val Lys Ser Ala Thr Ser Thr Ile Glu His
-85                   -80                   -75                   -70

Val Glu Ser Val Glu Pro Tyr Leu Pro Ile Tyr Arg Ile Asp Pro Gln
                   -65                   -60                   -55

Leu Phe Thr Lys Gly Ala Ser Glu Leu Val Lys Ala Val Ala Leu Asp
                   -50                   -45                   -40

Thr Lys Gln Lys Asn Lys Glu Val Gln Leu Arg Gly Ile Glu Gln Ile

-continued

```
            -35             -30             -25
Ala Gln Phe Ala Ile Ser Asn Asp Val Leu Tyr Ile Thr Ala Lys Pro
    -20             -15             -10

Glu Tyr Lys Val Met Asn Asp Val Ala Arg Gly Ile Val Lys Ala Asp
 -5          -1   1              5                  10

Val Ala Gln Ser Ser Tyr Gly Leu Tyr Gly Gln Gly Gln Ile Val Ala
             15              20              25

Val Ala Asp Thr Gly Leu Asp Thr Gly Arg Asn Asp Ser Ser Met His
         30              35              40

Glu Ala Phe Arg Gly Lys Ile Thr Ala Leu Tyr Ala Leu Gly Arg Thr
     45              50              55

Asn Asn Ala Asn Asp Thr Asn Gly His Gly Thr His Val Ala Gly Ser
60              65              70                  75

Val Leu Gly Asn Gly Ser Thr Asn Lys Gly Met Ala Pro Gln Ala Asn
             80              85              90

Leu Val Phe Gln Ser Ile Met Asp Ser Gly Gly Leu Gly Gly Leu
             95             100             105

Pro Ser Asn Leu Gln Thr Leu Phe Ser Gln Ala Tyr Ser Ala Gly Ala
            110             115             120

Arg Ile His Thr Asn Ser Trp Gly Ala Ala Val Asn Gly Ala Tyr Thr
            125             130             135

Thr Asp Ser Arg Asn Val Asp Asp Tyr Val Arg Lys Asn Asp Met Thr
140             145             150                 155

Ile Leu Phe Ala Ala Gly Asn Glu Gly Pro Asn Gly Gly Thr Ile Ser
            160             165             170

Ala Pro Gly Thr Ala Lys Asn Ala Ile Thr Val Gly Ala Thr Glu Asn
            175             180             185

Leu Arg Pro Ser Phe Gly Ser Tyr Ala Asp Asn Ile Asn His Val Ala
            190             195             200

Gln Phe Ser Ser Arg Gly Pro Thr Lys Asp Gly Arg Ile Lys Pro Asp
            205             210             215

Val Met Ala Pro Gly Thr Phe Ile Leu Ser Ala Arg Ser Ser Leu Ala
220             225             230                 235

Pro Asp Ser Ser Phe Trp Ala Asn His Asp Ser Lys Tyr Ala Tyr Met
            240             245             250

Gly Gly Thr Ser Met Ala Thr Pro Ile Val Ala Gly Asn Val Ala Gln
            255             260             265

Leu Arg Glu His Phe Val Lys Asn Arg Gly Ile Thr Pro Lys Pro Ser
            270             275             280

Leu Leu Lys Ala Ala Leu Ile Ala Gly Ala Ala Asp Ile Gly Leu Gly
            285             290             295

Tyr Pro Asn Gly Asn Gln Gly Trp Gly Arg Val Thr Leu Asp Lys Ser
300             305             310                 315

Leu Asn Val Ala Tyr Val Asn Glu Ser Ser Leu Ser Thr Ser Gln
            320             325             330

Lys Ala Thr Tyr Ser Phe Thr Ala Thr Ala Gly Lys Pro Leu Lys Ile
            335             340             345

Ser Leu Val Trp Ser Asp Ala Pro Ala Ser Thr Thr Ala Ser Val Thr
            350             355             360

Leu Val Asn Asp Leu Asp Leu Val Ile Thr Ala Pro Asn Gly Thr Gln
            365             370             375

Tyr Val Gly Asn Asp Phe Thr Ser Pro Tyr Asn Asp Asn Trp Asp Gly
380             385             390                 395
```

```
Arg Asn Asn Val Glu Asn Val Phe Ile Asn Ala Pro Gln Ser Gly Thr
                400                 405                 410
Tyr Thr Ile Glu Val Gln Ala Tyr Asn Val Pro Val Gly Pro Gln Thr
            415                 420                 425
Phe Ser Leu Ala Ile Val Asn
        430
```

<210> SEQ ID NO 3
<211> LENGTH: 434
<212> TYPE: PRT
<213> ORGANISM: Bacillus sp. KSM-KP43

<400> SEQUENCE: 3

```
Asn Asp Val Ala Arg Gly Ile Val Lys Ala Asp Val Ala Gln Ser Ser
1               5                   10                  15
Tyr Gly Leu Tyr Gly Gln Gly Gln Ile Val Ala Val Ala Asp Thr Gly
            20                  25                  30
Leu Asp Thr Gly Arg Asn Asp Ser Ser Met His Glu Ala Phe Arg Gly
        35                  40                  45
Lys Ile Thr Ala Leu Tyr Ala Leu Gly Arg Thr Asn Asn Ala Asn Asp
50                  55                  60
Thr Asn Gly His Gly Thr His Val Ala Gly Ser Val Leu Gly Asn Gly
65                  70                  75                  80
Ser Thr Asn Lys Gly Met Ala Pro Gln Ala Asn Leu Val Phe Gln Ser
                85                  90                  95
Ile Met Asp Ser Gly Gly Gly Leu Gly Gly Leu Pro Ser Asn Leu Gln
            100                 105                 110
Thr Leu Phe Ser Gln Ala Tyr Ser Ala Gly Ala Arg Ile His Thr Asn
        115                 120                 125
Ser Trp Gly Ala Ala Val Asn Gly Ala Tyr Thr Thr Asp Ser Arg Asn
130                 135                 140
Val Asp Asp Tyr Val Arg Lys Asn Asp Met Thr Ile Leu Phe Ala Ala
145                 150                 155                 160
Gly Asn Glu Gly Pro Asn Gly Gly Thr Ile Ser Ala Pro Gly Thr Ala
                165                 170                 175
Lys Asn Ala Ile Thr Val Gly Ala Thr Glu Asn Leu Arg Pro Ser Phe
            180                 185                 190
Gly Ser Tyr Ala Asp Asn Ile Asn His Val Ala Gln Phe Ser Ser Arg
        195                 200                 205
Gly Pro Thr Lys Asp Gly Arg Ile Lys Pro Asp Val Met Ala Pro Gly
210                 215                 220
Thr Phe Ile Leu Ser Ala Arg Ser Ser Leu Ala Pro Asp Ser Ser Phe
225                 230                 235                 240
Trp Ala Asn His Asp Ser Lys Tyr Ala Tyr Met Gly Gly Thr Ser Met
                245                 250                 255
Ala Thr Pro Ile Val Ala Gly Asn Val Ala Gln Leu Arg Glu His Phe
            260                 265                 270
Val Lys Asn Arg Gly Ile Thr Pro Lys Pro Ser Leu Leu Lys Ala Ala
        275                 280                 285
Leu Ile Ala Gly Ala Ala Asp Ile Gly Leu Gly Tyr Pro Asn Gly Asn
290                 295                 300
Gln Gly Trp Gly Arg Val Thr Leu Asp Lys Ser Leu Asn Val Ala Tyr
305                 310                 315                 320
Val Asn Glu Ser Ser Ser Leu Ser Thr Ser Gln Lys Ala Thr Tyr Ser
```

-continued

```
                    325                 330                 335
Phe Thr Ala Thr Ala Gly Lys Pro Leu Lys Ile Ser Leu Val Trp Ser
            340                 345                 350

Asp Ala Pro Ala Ser Thr Thr Ala Ser Val Thr Leu Val Asn Asp Leu
        355                 360                 365

Asp Leu Val Ile Thr Ala Pro Asn Gly Thr Gln Tyr Val Gly Asn Asp
    370                 375                 380

Phe Thr Ser Pro Tyr Asn Asp Asn Trp Asp Gly Arg Asn Asn Val Glu
385                 390                 395                 400

Asn Val Phe Ile Asn Ala Pro Gln Ser Gly Thr Tyr Thr Ile Glu Val
                405                 410                 415

Gln Ala Tyr Asn Val Pro Val Gly Pro Gln Thr Phe Ser Leu Ala Ile
            420                 425                 430

Val Asn

<210> SEQ ID NO 4
<211> LENGTH: 47
<212> TYPE: DNA
<213> ORGANISM: Artificial Sequence
<220> FEATURE:
<223> OTHER INFORMATION: Synthetic DNA

<400> SEQUENCE: 4
aaatggatcc gtgaggaggg aaccgaatga gaaagaagaa aaaggtg                47

<210> SEQ ID NO 5
<211> LENGTH: 21
<212> TYPE: DNA
<213> ORGANISM: Artificial Sequence
<220> FEATURE:
<223> OTHER INFORMATION: Synthetic DNA

<400> SEQUENCE: 5
attattcgtc cgtcccaatg c                                            21

<210> SEQ ID NO 6
<211> LENGTH: 34
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (15)..(17)
<223> OTHER INFORMATION: n is a, c, g, or t

<400> SEQUENCE: 6
ggacgaataa tgccnnngat ccgaatggtc atgg                              34

<210> SEQ ID NO 7
<211> LENGTH: 36
<212> TYPE: DNA
<213> ORGANISM: Artificial Sequence
<220> FEATURE:
<223> OTHER INFORMATION: Synthetic DNA

<400> SEQUENCE: 7
atattctaga cgattaccat attaattcct ctaccc                            36

<210> SEQ ID NO 8
<211> LENGTH: 21
<212> TYPE: DNA
<213> ORGANISM: Artificial Sequence
```

```
<220> FEATURE:
<223> OTHER INFORMATION: Synthetic DNA

<400> SEQUENCE: 8
ctatccatga tagattggaa g                                               21

<210> SEQ ID NO 9
<211> LENGTH: 38
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (16)..(18)
<223> OTHER INFORMATION: n is a, c, g, or t

<400> SEQUENCE: 9
tctatcatgg atagcnnngg gggacttgga ggactacc                             38

<210> SEQ ID NO 10
<211> LENGTH: 20
<212> TYPE: DNA
<213> ORGANISM: Artificial Sequence
<220> FEATURE:
<223> OTHER INFORMATION: Synthetic DNA

<400> SEQUENCE: 10
gctccccagg agtttgtatg                                                 20

<210> SEQ ID NO 11
<211> LENGTH: 37
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (18)..(20)
<223> OTHER INFORMATION: n is a, c, g, or t

<400> SEQUENCE: 11
caaactcctg gggagcannn gtgaatgggg cttacac                              37

<210> SEQ ID NO 12
<211> LENGTH: 40
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (21)..(23)
<223> OTHER INFORMATION: n is a, c, g, or t

<400> SEQUENCE: 12
caaactcctg gggagcagca nnngtgaatg gggcttacac                           40

<210> SEQ ID NO 13
<211> LENGTH: 40
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (18)..(23)
<223> OTHER INFORMATION: n is a, c, g, or t
```

```
<400> SEQUENCE: 13
caaactcctg gggagcannn nnngtgaatg gggcttacac                    40

<210> SEQ ID NO 14
<211> LENGTH: 40
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (18)..(26)
<223> OTHER INFORMATION: n is a, c, g, or t

<400> SEQUENCE: 14
caaactcctg gggagcannn nnnnnaatg gggcttacac                     40

<210> SEQ ID NO 15
<211> LENGTH: 43
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (18)..(29)
<223> OTHER INFORMATION: n is a, c, g, or t

<400> SEQUENCE: 15
caaactcctg gggagcannn nnnnnnnnng gggcttacac aac                43

<210> SEQ ID NO 16
<211> LENGTH: 23
<212> TYPE: DNA
<213> ORGANISM: Artificial Sequence
<220> FEATURE:
<223> OTHER INFORMATION: Synthetic DNA

<400> SEQUENCE: 16
tccccaggag tttgtatgaa ttc                                     23

<210> SEQ ID NO 17
<211> LENGTH: 40
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (15)..(17)
<223> OTHER INFORMATION: n is a, c, g, or t
<220> FEATURE:
<221> NAME/KEY: misc_feature
<222> LOCATION: (21)..(23)
<223> OTHER INFORMATION: n is a, c, g, or t

<400> SEQUENCE: 17
caaactcctg gggannngca nnngtgaatg gggcttacac                    40

<210> SEQ ID NO 18
<211> LENGTH: 40
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (15)..(23)
<223> OTHER INFORMATION: n is a, c, g, or t
```

<400> SEQUENCE: 18
caaactcctg gggannnnnn nngtgaatg gggcttacac                            40

<210> SEQ ID NO 19
<211> LENGTH: 433
<212> TYPE: PRT
<213> ORGANISM: Bacillus sp. KSM-KP9860

<400> SEQUENCE: 19

```
Asp Val Ala Arg Gly Ile Val Lys Ala Asp Val Ala Gln Ser Ser Tyr
1               5                   10                  15

Gly Leu Tyr Gly Gln Gly Gln Ile Val Ala Val Ala Asp Thr Gly Leu
            20                  25                  30

Asp Thr Gly Arg Asn Asp Ser Ser Met His Glu Ala Phe Arg Gly Lys
        35                  40                  45

Ile Thr Ala Leu Tyr Ala Leu Gly Arg Thr Asn Asn Ala Asn Asp Thr
    50                  55                  60

Asn Gly His Gly Thr His Val Ala Gly Ser Val Leu Gly Asn Gly Ala
65                  70                  75                  80

Thr Asn Lys Gly Met Ala Pro Gln Ala Asn Leu Val Phe Gln Ser Ile
                85                  90                  95

Met Asp Ser Ser Gly Gly Leu Gly Leu Pro Ser Asn Leu Gln Thr
            100                 105                 110

Leu Phe Ser Gln Ala Phe Ser Ala Gly Ala Arg Ile His Thr Asn Ser
        115                 120                 125

Trp Gly Ala Ala Val Asn Gly Ala Tyr Thr Thr Asp Ser Arg Asn Val
    130                 135                 140

Asp Asp Tyr Val Arg Lys Asn Asp Met Thr Ile Leu Phe Ala Ala Gly
145                 150                 155                 160

Asn Glu Arg Pro Asn Gly Gly Thr Ile Ser Ala Pro Gly Thr Ala Lys
                165                 170                 175

Asn Ala Ile Thr Val Gly Ala Thr Glu Asn Leu Arg Pro Ser Phe Gly
            180                 185                 190

Ser Tyr Ala Asp Asn Ile Asn His Val Ala Gln Phe Ser Ser Arg Gly
        195                 200                 205

Pro Thr Lys Asp Gly Arg Ile Lys Pro Asp Val Met Ala Pro Gly Thr
    210                 215                 220

Tyr Ile Leu Ser Ala Arg Ser Ser Leu Ala Pro Asp Ser Ser Phe Trp
225                 230                 235                 240

Ala Asn His Asp Ser Lys Tyr Ala Tyr Met Gly Gly Thr Ser Met Ala
                245                 250                 255

Thr Pro Ile Val Ala Gly Asn Val Ala Gln Leu Arg Glu His Phe Val
            260                 265                 270

Lys Asn Arg Gly Ile Thr Pro Lys Pro Ser Leu Leu Lys Ala Ala Leu
        275                 280                 285

Ile Ala Gly Ala Ala Asp Val Gly Leu Gly Tyr Pro Asn Gly Asn Gln
    290                 295                 300

Gly Trp Gly Arg Val Thr Leu Asp Lys Ser Leu Asn Val Ala Tyr Val
305                 310                 315                 320

Asn Glu Ser Ser Ala Leu Ser Thr Ser Gln Lys Ala Thr Tyr Thr Phe
                325                 330                 335

Thr Ala Thr Ala Gly Lys Pro Leu Lys Ile Ser Leu Val Trp Ser Asp
            340                 345                 350
```

```
Ala Pro Ala Ser Thr Thr Ala Ser Val Thr Leu Val Asn Asp Leu Asp
            355                 360                 365

Leu Val Ile Thr Ala Pro Asn Gly Thr Arg Tyr Val Gly Asn Asp Phe
        370                 375                 380

Ser Ala Pro Phe Asp Asn Asn Trp Asp Gly Arg Asn Asn Val Glu Asn
385                 390                 395                 400

Val Phe Ile Asn Ser Pro Gln Ser Gly Thr Tyr Thr Ile Glu Val Gln
                405                 410                 415

Ala Tyr Asn Val Pro Val Gly Pro Gln Asn Phe Ser Leu Ala Ile Val
                420                 425                 430

Asn

<210> SEQ ID NO 20
<211> LENGTH: 433
<212> TYPE: PRT
<213> ORGANISM: Bacillus No. D-6

<400> SEQUENCE: 20

Asn Asp Val Ala Arg Gly Ile Val Lys Ala Asp Val Ala Gln Asn Asn
1               5                   10                  15

Tyr Gly Leu Tyr Gly Gln Gly Gln Val Val Ala Val Ala Asp Thr Gly
            20                  25                  30

Leu Asp Thr Gly Arg Asn Asp Ser Ser Met His Glu Ala Phe Arg Gly
        35                  40                  45

Lys Ile Thr Ala Leu Tyr Ala Leu Gly Arg Thr Asn Asn Ala Asn Asp
    50                  55                  60

Pro Asn Gly His Gly Thr His Val Ala Gly Ser Val Leu Gly Asn Ala
65                  70                  75                  80

Leu Asn Lys Gly Met Ala Pro Gln Ala Asn Leu Val Phe Gln Ser Ile
                85                  90                  95

Met Asp Ser Ser Gly Gly Leu Gly Gly Leu Pro Ser Asn Leu Asn Thr
            100                 105                 110

Leu Phe Ser Gln Ala Trp Asn Ala Gly Ala Arg Ile His Thr Asn Ser
        115                 120                 125

Trp Gly Ala Pro Val Asn Gly Ala Tyr Thr Ala Asn Ser Arg Gln Val
    130                 135                 140

Asp Glu Tyr Val Arg Asn Asn Asp Met Thr Val Leu Phe Ala Ala Gly
145                 150                 155                 160

Asn Glu Gly Pro Asn Ser Gly Thr Ile Ser Ala Pro Gly Thr Ala Lys
                165                 170                 175

Asn Ala Ile Thr Val Gly Ala Thr Glu Asn Tyr Arg Pro Ser Phe Gly
            180                 185                 190

Ser Ile Ala Asp Asn Pro Asn His Ile Ala Gln Phe Ser Ser Arg Gly
        195                 200                 205

Ala Thr Arg Asp Gly Arg Ile Lys Pro Asp Val Thr Ala Pro Gly Thr
    210                 215                 220

Phe Ile Leu Ser Ala Arg Ser Ser Leu Ala Pro Asp Ser Ser Phe Trp
225                 230                 235                 240

Ala Asn Tyr Asn Ser Lys Tyr Ala Tyr Met Gly Gly Thr Ser Met Ala
                245                 250                 255

Thr Pro Ile Val Ala Gly Asn Val Ala Gln Leu Arg Glu His Phe Ile
            260                 265                 270

Lys Asn Arg Gly Ile Thr Pro Lys Pro Ser Leu Ile Lys Ala Ala Leu
        275                 280                 285
```

```
Ile Ala Gly Ala Thr Asp Val Gly Leu Gly Tyr Pro Ser Gly Asp Gln
    290                 295                 300

Gly Trp Gly Arg Val Thr Leu Asp Lys Ser Leu Asn Val Ala Tyr Val
305                 310                 315                 320

Asn Glu Ala Thr Ala Leu Thr Thr Gly Gln Lys Ala Thr Tyr Ser Phe
                325                 330                 335

Gln Thr Gln Ala Gly Lys Pro Leu Lys Ile Ser Leu Val Trp Thr Asp
            340                 345                 350

Ala Pro Gly Ser Thr Thr Ala Ser Tyr Thr Leu Val Asn Asp Leu Asp
        355                 360                 365

Leu Val Ile Thr Ala Pro Asn Gly Gln Lys Tyr Val Gly Asn Asp Phe
    370                 375                 380

Ser Tyr Pro Tyr Asp Asn Asn Trp Asp Gly Arg Asn Asn Val Glu Asn
385                 390                 395                 400

Val Phe Ile Asn Ala Pro Gln Ser Gly Thr Tyr Thr Ile Glu Val Gln
                405                 410                 415

Ala Tyr Asn Val Pro Ser Gly Pro Gln Arg Phe Ser Leu Ala Ile Val
            420                 425                 430

His

<210> SEQ ID NO 21
<211> LENGTH: 433
<212> TYPE: PRT
<213> ORGANISM: Bacillus sp. Y

<400> SEQUENCE: 21

Asn Asp Val Ala Arg Gly Ile Val Lys Ala Asp Val Ala Gln Asn Asn
1               5                   10                  15

Tyr Gly Leu Tyr Gly Gln Gly Gln Val Val Ala Val Ala Asp Thr Gly
            20                  25                  30

Leu Asp Thr Gly Arg Asn Asp Ser Ser Met His Glu Ala Phe Arg Gly
        35                  40                  45

Lys Ile Thr Ala Leu Tyr Ala Leu Gly Arg Thr Asn Asn Ala Ser Asp
    50                  55                  60

Pro Asn Gly His Gly Thr His Val Ala Gly Ser Val Leu Gly Asn Ala
65                  70                  75                  80

Leu Asn Lys Gly Met Ala Pro Gln Ala Asn Leu Val Phe Gln Ser Ile
                85                  90                  95

Met Asp Ser Ser Gly Gly Leu Gly Leu Pro Ser Asn Leu Asn Thr
            100                 105                 110

Leu Phe Ser Gln Ala Trp Asn Ala Gly Ala Arg Ile His Thr Asn Ser
        115                 120                 125

Trp Gly Ala Pro Val Asn Gly Ala Tyr Thr Ala Asn Ser Arg Gln Val
    130                 135                 140

Asp Glu Tyr Val Arg Asn Asn Asp Met Thr Val Leu Phe Ala Ala Gly
145                 150                 155                 160

Asn Glu Gly Pro Asn Ser Gly Thr Ile Ser Ala Pro Gly Thr Ala Lys
                165                 170                 175

Asn Ala Ile Thr Val Gly Ala Thr Glu Asn Tyr Arg Pro Ser Phe Gly
            180                 185                 190

Ser Ile Ala Asp Asn Pro Asn His Ile Ala Gln Phe Ser Ser Arg Gly
        195                 200                 205

Ala Thr Arg Asp Gly Arg Ile Lys Pro Asp Val Thr Ala Pro Gly Thr
    210                 215                 220
```

```
Phe Ile Leu Ser Ala Arg Ser Ser Leu Ala Pro Asp Ser Ser Phe Trp
225                 230                 235                 240

Ala Asn Tyr Asn Ser Lys Tyr Ala Tyr Met Gly Gly Thr Ser Met Ala
                245                 250                 255

Thr Pro Ile Val Ala Gly Asn Val Ala Gln Leu Arg Glu His Phe Ile
            260                 265                 270

Lys Asn Arg Gly Ile Thr Pro Lys Pro Ser Leu Ile Lys Ala Ala Leu
        275                 280                 285

Ile Ala Gly Ala Thr Asp Val Gly Leu Gly Tyr Pro Asn Gly Asp Gln
    290                 295                 300

Gly Trp Gly Arg Val Thr Leu Asn Lys Ser Leu Asn Val Ala Tyr Val
305                 310                 315                 320

Asn Glu Ala Thr Ala Leu Ala Thr Gly Gln Lys Ala Thr Tyr Ser Phe
                325                 330                 335

Gln Ala Gln Ala Gly Lys Pro Leu Lys Ile Ser Leu Val Trp Thr Asp
            340                 345                 350

Ala Pro Gly Ser Thr Thr Ala Ser Tyr Thr Leu Val Asn Asp Leu Asp
        355                 360                 365

Leu Val Ile Thr Ala Pro Asn Gly Gln Lys Tyr Val Gly Asn Asp Phe
370                 375                 380

Ser Tyr Pro Tyr Asp Asn Asn Trp Asp Gly Arg Asn Asn Val Glu Asn
385                 390                 395                 400

Val Phe Ile Asn Ala Pro Gln Ser Gly Thr Tyr Ile Ile Glu Val Gln
                405                 410                 415

Ala Tyr Asn Val Pro Ser Gly Pro Gln Arg Phe Ser Leu Ala Ile Val
            420                 425                 430

His

<210> SEQ ID NO 22
<211> LENGTH: 433
<212> TYPE: PRT
<213> ORGANISM: Bacillus SD521

<400> SEQUENCE: 22

Asn Asp Val Ala Arg Gly Ile Val Lys Ala Asp Val Ala Gln Asn Asn
1               5                   10                  15

Tyr Gly Leu Tyr Gly Gln Gly Val Val Ala Val Ala Asp Thr Gly
                20                  25                  30

Leu Asp Thr Gly Arg Asn Asp Ser Ser Met His Glu Ala Phe Arg Gly
            35                  40                  45

Lys Ile Thr Ala Leu Tyr Ala Leu Gly Arg Thr Asn Asn Ala Asn Asp
        50                  55                  60

Pro Asn Gly His Gly Thr His Val Ala Gly Ser Val Leu Gly Asn Ala
65                  70                  75                  80

Leu Asn Lys Gly Met Ala Pro Gln Ala Asn Leu Val Phe Gln Ser Ile
                85                  90                  95

Met Asp Ser Ser Gly Leu Gly Gly Leu Pro Ser Asn Leu Asn Thr
            100                 105                 110

Leu Phe Ser Gln Ala Trp Asn Ala Gly Ala Arg Ile His Thr Asn Ser
        115                 120                 125

Trp Gly Ala Pro Val Asn Gly Ala Tyr Thr Ala Asn Ser Arg Gln Val
    130                 135                 140

Asp Glu Tyr Val Arg Asn Asn Asp Met Thr Val Leu Phe Ala Ala Gly
145                 150                 155                 160
```

Asn Glu Gly Pro Asn Ser Gly Thr Ile Ser Ala Pro Gly Thr Ala Lys
            165                 170                 175

Asn Ala Ile Thr Val Gly Ala Thr Glu Asn Tyr Arg Pro Ser Phe Gly
        180                 185                 190

Ser Leu Ala Asp Asn Pro Asn His Ile Ala Gln Phe Ser Arg Gly
            195                 200                 205

Ala Thr Arg Asp Gly Arg Ile Lys Pro Asp Val Thr Ala Pro Gly Thr
    210                 215                 220

Phe Ile Leu Ser Ala Arg Ser Ser Leu Ala Pro Asp Ser Ser Phe Trp
225                 230                 235                 240

Ala Asn Tyr Asn Ser Lys Tyr Ala Tyr Met Gly Gly Thr Ser Met Ala
                245                 250                 255

Thr Pro Ile Val Ala Gly Asn Val Ala Gln Leu Arg Glu His Phe Ile
            260                 265                 270

Lys Asn Arg Gly Ile Thr Pro Lys Pro Ser Leu Ile Lys Ala Ala Leu
        275                 280                 285

Ile Ala Gly Ala Thr Asp Val Gly Leu Gly Tyr Pro Ser Gly Asp Gln
    290                 295                 300

Gly Trp Gly Arg Val Thr Leu Asp Lys Ser Leu Asn Val Ala Tyr Val
305                 310                 315                 320

Asn Glu Ala Thr Ala Leu Ala Thr Gly Gln Lys Ala Thr Tyr Ser Phe
                325                 330                 335

Gln Ala Gln Ala Gly Lys Pro Leu Lys Ile Ser Leu Val Trp Thr Asp
            340                 345                 350

Ala Pro Gly Ser Thr Thr Ala Ser Tyr Thr Leu Val Asn Asp Leu Asp
        355                 360                 365

Leu Val Ile Thr Ala Pro Asn Gly Gln Lys Tyr Val Gly Asn Asp Phe
    370                 375                 380

Ser Tyr Pro Tyr Asp Asn Asn Trp Asp Gly Arg Asn Asn Val Glu Asn
385                 390                 395                 400

Val Phe Ile Asn Ala Pro Gln Ser Gly Thr Tyr Thr Ile Glu Val Gln
                405                 410                 415

Ala Tyr Asn Val Pro Ser Gly Pro Gln Arg Phe Ser Leu Ala Ile Val
            420                 425                 430

His

<210> SEQ ID NO 23
<211> LENGTH: 434
<212> TYPE: PRT
<213> ORGANISM: Bacillus sp. NV1

<400> SEQUENCE: 23

Asn Asp Val Ala Arg Gly Ile Val Lys Ala Asp Val Ala Gln Ser Ser
1               5                   10                  15

Tyr Gly Leu Tyr Gly Gln Gly Gln Val Val Ala Val Ala Asp Thr Gly
                20                  25                  30

Leu Asp Thr Gly Arg Asn Asp Ser Ser Met His Glu Ala Phe Arg Gly
            35                  40                  45

Lys Ile Thr Ala Ile Tyr Ala Leu Gly Arg Thr Asn Asn Ala Asn Asp
        50                  55                  60

Pro Asn Gly His Gly Thr His Val Ala Gly Ser Val Leu Gly Asn Gly
65                  70                  75                  80

Thr Ser Asn Lys Gly Met Ala Pro Gln Ala Asn Leu Val Phe Gln Ser
                85                  90                  95

```
Val Met Asp Ser Asn Gly Gly Leu Gly Gly Leu Pro Ser Asn Val Ser
            100                 105                 110

Thr Leu Phe Ser Gln Ala Tyr Ser Gly Ala Arg Ile His Thr Asn
        115                 120                 125

Ser Trp Gly Ala Pro Val Asn Gly Ala Tyr Thr Thr Asp Ser Arg Asn
130                 135                 140

Val Asp Asp Tyr Val Arg Lys Asn Asp Met Ala Val Leu Phe Ala Ala
145                 150                 155                 160

Gly Asn Glu Gly Pro Asn Gly Gly Thr Ile Ser Ala Pro Gly Thr Ala
                165                 170                 175

Lys Asn Ala Ile Thr Val Gly Ala Thr Glu Asn Leu Arg Pro Ser Phe
                180                 185                 190

Gly Ser Tyr Ala Asp Asn Ile Asn His Val Ala Gln Phe Ser Ser Arg
            195                 200                 205

Gly Pro Thr Lys Asp Gly Arg Ile Lys Pro Asp Val Met Ala Pro Gly
        210                 215                 220

Thr Phe Ile Leu Ser Ala Arg Ser Ser Leu Ala Pro Asp Ser Ser Phe
225                 230                 235                 240

Trp Ala Asn His Asp Ser Lys Tyr Ala Tyr Met Gly Gly Thr Ser Met
                245                 250                 255

Ala Thr Pro Ile Val Ala Gly Asn Val Ala Gln Leu Arg Glu His Phe
                260                 265                 270

Ile Lys Asn Arg Gly Ile Thr Pro Lys Pro Ser Leu Leu Lys Ala Ala
            275                 280                 285

Leu Ile Ala Gly Ala Thr Asp Ile Gly Leu Gly Tyr Pro Ser Gly Asn
        290                 295                 300

Gln Gly Trp Gly Arg Val Thr Leu Asp Lys Ser Leu Asn Val Ala Phe
305                 310                 315                 320

Val Asn Glu Thr Ser Ser Leu Ser Thr Asn Gln Lys Ala Thr Tyr Ser
                325                 330                 335

Phe Thr Ala Gln Ser Gly Lys Pro Leu Lys Ile Ser Leu Val Trp Ser
                340                 345                 350

Asp Ala Pro Ala Ser Thr Ser Ala Ser Val Thr Leu Val Asn Asp Leu
            355                 360                 365

Asp Leu Val Ile Thr Ala Pro Asn Gly Thr Lys Tyr Val Gly Asn Asp
        370                 375                 380

Phe Thr Ala Pro Tyr Asp Asn Asn Trp Asp Gly Arg Asn Asn Val Glu
385                 390                 395                 400

Asn Val Phe Ile Asn Ala Pro Gln Ser Gly Thr Tyr Thr Val Glu Val
                405                 410                 415

Gln Ala Tyr Asn Val Pro Gln Gly Pro Gln Ala Phe Ser Leu Ala Ile
                420                 425                 430

Val Asn

<210> SEQ ID NO 24
<211> LENGTH: 433
<212> TYPE: PRT
<213> ORGANISM: NCIB12513

<400> SEQUENCE: 24

Asn Asp Val Ala Arg Gly Ile Val Lys Ala Asp Val Ala Gln Asn Asn
1               5                   10                  15

Phe Gly Leu Tyr Gly Gln Gly Gln Ile Val Ala Val Ala Asp Thr Gly
                20                  25                  30
```

```
Leu Asp Thr Gly Arg Asn Asp Ser Ser Met His Glu Ala Phe Arg Gly
         35                  40                  45

Lys Ile Thr Ala Leu Tyr Ala Leu Gly Arg Thr Asn Asn Ala Asn Asp
     50                  55                  60

Pro Asn Gly His Gly Thr His Val Ala Gly Ser Val Leu Gly Asn Ala
 65                  70                  75                  80

Thr Asn Lys Gly Met Ala Pro Gln Ala Asn Leu Val Phe Gln Ser Ile
                 85                  90                  95

Met Asp Ser Gly Gly Leu Gly Gly Leu Pro Ala Asn Leu Gln Thr
                100                 105                 110

Leu Phe Ser Gln Ala Tyr Ser Ala Gly Ala Arg Ile His Thr Asn Ser
         115                 120                 125

Trp Gly Ala Pro Val Asn Gly Ala Tyr Thr Thr Asp Ser Arg Asn Val
     130                 135                 140

Asp Asp Tyr Val Arg Lys Asn Asp Met Thr Ile Leu Phe Ala Ala Gly
145                 150                 155                 160

Asn Glu Gly Pro Gly Ser Gly Thr Ile Ser Ala Pro Gly Thr Ala Lys
                165                 170                 175

Asn Ala Ile Thr Val Gly Ala Thr Glu Asn Leu Arg Pro Ser Phe Gly
            180                 185                 190

Ser Tyr Ala Asp Asn Ile Asn His Val Ala Gln Phe Ser Ser Arg Gly
        195                 200                 205

Pro Thr Lys Asp Gly Arg Ile Lys Pro Asp Val Met Ala Pro Gly Thr
    210                 215                 220

Tyr Ile Leu Ser Ala Arg Ser Ser Leu Ala Pro Asp Ser Ser Phe Trp
225                 230                 235                 240

Ala Asn His Asp Ser Lys Tyr Ala Tyr Met Gly Gly Thr Ser Met Ala
                245                 250                 255

Thr Pro Ile Val Ala Gly Asn Val Ala Gln Leu Arg Glu His Phe Val
            260                 265                 270

Lys Asn Arg Gly Val Thr Pro Lys Pro Ser Leu Leu Lys Ala Ala Leu
        275                 280                 285

Ile Ala Gly Ala Ala Asp Val Gly Leu Gly Phe Pro Asn Gly Asn Gln
    290                 295                 300

Gly Trp Gly Arg Val Thr Leu Asp Lys Ser Leu Asn Val Ala Phe Val
305                 310                 315                 320

Asn Glu Thr Ser Pro Leu Ser Thr Ser Gln Lys Ala Thr Tyr Ser Phe
                325                 330                 335

Thr Ala Gln Ala Gly Lys Pro Leu Lys Ile Ser Leu Val Trp Ser Asp
            340                 345                 350

Ala Pro Gly Ser Thr Thr Ala Ser Leu Thr Leu Val Asn Asp Leu Asp
        355                 360                 365

Leu Val Ile Thr Ala Pro Asn Gly Thr Lys Tyr Val Gly Asn Asp Phe
    370                 375                 380

Thr Ala Pro Tyr Asp Asn Asn Trp Asp Gly Arg Asn Asn Val Glu Asn
385                 390                 395                 400

Val Phe Ile Asn Ala Pro Gln Ser Gly Thr Tyr Thr Val Glu Val Gln
                405                 410                 415

Ala Tyr Asn Val Pro Gln Ser Pro Gln Thr Phe Ser Leu Ala Ile Val
            420                 425                 430

His

<210> SEQ ID NO 25
```

```
<211> LENGTH: 434
<212> TYPE: PRT
<213> ORGANISM: Bacillus sp. KSM-9865

<400> SEQUENCE: 25
```

| | | | | | | | | | | | | | | |
|---|---|---|---|---|---|---|---|---|---|---|---|---|---|---|
| Asn | Asp | Val | Ala | Arg | Gly | Ile | Val | Lys | Ala | Asp | Val | Ala | Gln | Ser | Ser |
| 1 | | | | 5 | | | | | 10 | | | | | 15 | |
| Tyr | Gly | Leu | Tyr | Gly | Gln | Gly | Gln | Ile | Val | Ala | Val | Ala | Asp | Thr | Gly |
| | | | 20 | | | | | 25 | | | | | 30 | | |
| Leu | Asp | Thr | Gly | Arg | Asn | Asp | Ser | Ser | Met | His | Glu | Ala | Phe | Arg | Gly |
| | | | 35 | | | | | 40 | | | | | 45 | | |
| Lys | Ile | Thr | Ala | Leu | Tyr | Ala | Leu | Gly | Arg | Thr | Asn | Asn | Ala | Asn | Asp |
| | 50 | | | | | 55 | | | | | 60 | | | | |
| Thr | Asn | Gly | His | Gly | Thr | His | Val | Ala | Gly | Ser | Val | Leu | Gly | Asn | Gly |
| 65 | | | | | 70 | | | | | 75 | | | | | 80 |
| Ser | Thr | Asn | Lys | Gly | Met | Ala | Pro | Gln | Ala | Asn | Leu | Val | Phe | Gln | Ser |
| | | | | 85 | | | | | 90 | | | | | 95 | |
| Ile | Met | Asp | Ser | Gly | Gly | Gly | Leu | Gly | Gly | Leu | Pro | Ser | Asn | Leu | Gln |
| | | | | 100 | | | | | 105 | | | | | 110 | |
| Thr | Leu | Phe | Ser | Gln | Ala | Tyr | Ser | Ala | Gly | Ala | Arg | Ile | His | Thr | Asn |
| | | | 115 | | | | | 120 | | | | | 125 | | |
| Ser | Trp | Gly | Ala | Ala | Val | Asn | Gly | Ala | Tyr | Thr | Thr | Asp | Ser | Arg | Asn |
| | 130 | | | | | 135 | | | | | 140 | | | | |
| Val | Asp | Asp | Tyr | Val | Arg | Lys | Asn | Asp | Met | Thr | Ile | Leu | Phe | Ala | Ala |
| 145 | | | | | 150 | | | | | 155 | | | | | 160 |
| Gly | Asn | Glu | Gly | Pro | Asn | Gly | Gly | Thr | Ile | Ser | Ala | Pro | Gly | Thr | Ala |
| | | | | 165 | | | | | 170 | | | | | 175 | |
| Lys | Asn | Ala | Ile | Thr | Val | Gly | Ala | Thr | Glu | Asn | Leu | Arg | Pro | Ser | Phe |
| | | | 180 | | | | | 185 | | | | | 190 | | |
| Gly | Ser | Tyr | Ala | Asp | Asn | Ile | Asn | His | Val | Ala | Gln | Phe | Ser | Ser | Arg |
| | | | 195 | | | | | 200 | | | | | 205 | | |
| Gly | Pro | Thr | Lys | Asp | Gly | Arg | Ile | Lys | Pro | Asp | Val | Met | Ala | Pro | Gly |
| | 210 | | | | | 215 | | | | | 220 | | | | |
| Thr | Phe | Ile | Leu | Ser | Ala | Arg | Ser | Ser | Leu | Ala | Pro | Asp | Ser | Ser | Phe |
| 225 | | | | | 230 | | | | | 235 | | | | | 240 |
| Trp | Ala | Asn | His | Asp | Ser | Lys | Tyr | Ala | Tyr | Met | Gly | Gly | Thr | Ser | Met |
| | | | | 245 | | | | | 250 | | | | | 255 | |
| Ala | Thr | Pro | Ile | Val | Ala | Gly | Asn | Val | Ala | Gln | Leu | Arg | Glu | His | Phe |
| | | | 260 | | | | | 265 | | | | | 270 | | |
| Val | Lys | Asn | Arg | Gly | Ile | Thr | Pro | Lys | Pro | Ser | Leu | Leu | Lys | Ala | Ala |
| | | | 275 | | | | | 280 | | | | | 285 | | |
| Leu | Ile | Ala | Gly | Ala | Ala | Asp | Ile | Gly | Leu | Gly | Tyr | Pro | Asn | Gly | Asn |
| | 290 | | | | | 295 | | | | | 300 | | | | |
| Gln | Gly | Trp | Gly | Arg | Val | Thr | Leu | Asp | Lys | Ser | Leu | Asn | Val | Ala | Tyr |
| 305 | | | | | 310 | | | | | 315 | | | | | 320 |
| Val | Asn | Glu | Ser | Ser | Ser | Leu | Ser | Thr | Ser | Gln | Lys | Ala | Thr | Tyr | Ser |
| | | | | 325 | | | | | 330 | | | | | 335 | |
| Phe | Thr | Ala | Thr | Ala | Gly | Lys | Pro | Leu | Lys | Ile | Ser | Leu | Val | Trp | Ser |
| | | | 340 | | | | | 345 | | | | | 350 | | |
| Asp | Ala | Pro | Ala | Ser | Thr | Thr | Ala | Ser | Val | Thr | Leu | Val | Asn | Asp | Leu |
| | | | 355 | | | | | 360 | | | | | 365 | | |
| Asp | Leu | Val | Ile | Thr | Ala | Pro | Asn | Gly | Thr | Gln | Tyr | Val | Gly | Asn | Asp |
| | 370 | | | | | 375 | | | | | 380 | | | | |
| Phe | Thr | Ser | Pro | Tyr | Asn | Asn | Asn | Trp | Asp | Gly | Arg | Asn | Asn | Val | Glu |

-continued

```
            385                 390                 395                 400
Asn Val Phe Ile Asn Ala Pro Gln Ser Gly Thr Tyr Thr Ile Glu Val
                405                 410                 415

Gln Ala Tyr Asn Val Pro Val Gly Pro Gln Thr Phe Ser Leu Ala Ile
                420                 425                 430

Val Asn
```